US011896635B2

(12) United States Patent
Kosai et al.

(10) Patent No.: US 11,896,635 B2
(45) Date of Patent: Feb. 13, 2024

(54) ONCOLYTIC VIRUS (ONCOLYTIC IMMUNOTHERAPY) CAPABLE OF EFFECTIVELY TREATING EVEN METASTATIC CANCER WHILE ENSURING SAFETY, WITH EXPRESSION CONTROL SYSTEM PROVIDING OPTIMAL EXPRESSION LEVEL OF MOUNTED IMMUNOGENIC GENE

(71) Applicant: KAGOSHIMA UNIVERSITY, Kagoshima (JP)

(72) Inventors: Ken-ichiro Kosai, Kagoshima (JP); Nobuhiro Ijichi, Kagoshima (JP)

(73) Assignee: KAGOSHIMA UNIVERSITY, Kagoshima (JP)

( * ) Notice: Subject to any disclaimer, the term of this patent is extended or adjusted under 35 U.S.C. 154(b) by 488 days.

(21) Appl. No.: 16/758,019

(22) PCT Filed: Nov. 8, 2018

(86) PCT No.: PCT/JP2018/041541
§ 371 (c)(1),
(2) Date: Apr. 21, 2020

(87) PCT Pub. No.: WO2019/093435
PCT Pub. Date: May 16, 2019

(65) Prior Publication Data
US 2021/0008134 A1    Jan. 14, 2021

(30) Foreign Application Priority Data

Nov. 8, 2017  (JP) .................................. 2017-215579
Mar. 19, 2018 (JP) .................................. 2018-050722

(51) Int. Cl.
*C12N 7/00* (2006.01)
*A61K 35/761* (2015.01)
(Continued)

(52) U.S. Cl.
CPC ............ *A61K 35/761* (2013.01); *A61P 35/04* (2018.01); *C12N 15/86* (2013.01); *C12N 15/861* (2013.01)

(58) Field of Classification Search
None
See application file for complete search history.

(56) References Cited

U.S. PATENT DOCUMENTS 6,544,780 B1 * 4/2003 Wang ................... A61K 39/292
424/188.1
8,142,770 B2 * 3/2012 Kamizono ............... A61P 35/00
435/91.42
(Continued)

FOREIGN PATENT DOCUMENTS

AU    2003265873 A1    4/2005
CN    102548584 A      7/2012
(Continued)

OTHER PUBLICATIONS

International Preliminary Report on Patentability (translation) for PCT/JP2018/041541, dated May 14, 2020, 12 pages.
(Continued)

*Primary Examiner* — M Franco G Salvoza
(74) *Attorney, Agent, or Firm* — MORRISON & FOERSTER LLP

(57) ABSTRACT

The present invention is based on a novel concept for finding the optimum expression level of a therapeutic gene for inducing the largest therapeutic effect without any adverse reaction. An object of the present invention is to develop an immuno-viral therapeutic vector exerting the optimal therapeutic effect while ensuring high safety. The present invention provides, for example, an oncolytic virus comprising an immunity-inducing gene operably linked to the downstream of E2F promoter or a promoter having an activity equivalent thereto, wherein at least one promoter for nucleic acids (Continued)

encoding an element essential for viral replication or assembly is replaced with a promoter for an organ specific highly expressed factor or with a promoter for a cancer cell specific highly expressed factor.

7 Claims, 11 Drawing Sheets

Specification includes a Sequence Listing.

(51) Int. Cl.
*A61P 35/04* (2006.01)
*C12N 15/86* (2006.01)
*C12N 15/861* (2006.01)

(56) References Cited

U.S. PATENT DOCUMENTS

| | | | | |
|---|---|---|---|---|
| 2005/0186178 | A1* | 8/2005 | Ennist | A61K 35/761 435/235.1 |
| 2007/0036759 | A1 | 2/2007 | Kosai et al. | |
| 2012/0148535 | A1 | 6/2012 | Carrió et al. | |
| 2013/0108665 | A1 | 5/2013 | Liang | |
| 2013/0309203 | A1 | 11/2013 | Kosai | |
| 2015/0232880 | A1 | 8/2015 | Hemminki et al. | |
| 2018/0221423 | A1* | 8/2018 | O'Shea | A61K 35/761 |

FOREIGN PATENT DOCUMENTS

| | | | | |
|---|---|---|---|---|
| CN | 102985094 | A | 3/2013 | |
| CN | 105177045 | | 12/2015 | |
| CN | 105307671 | | 2/2016 | |
| EP | 1662004 | A1 | 5/2006 | |
| EP | 2428229 | A1 | 3/2012 | |
| EP | 2603223 | A1 | 6/2013 | |
| JP | 4478775 | B2 | 6/2010 | |
| JP | 2012-525833 | A | 10/2012 | |
| JP | 2013-532977 | A | 8/2013 | |
| JP | 2016-522805 | | 8/2016 | |
| JP | 5963363 | B2 | 8/2016 | |
| KR | 10-2012-0049185 | A | 5/2012 | |
| WO | WO-0123004 | A1 * | 4/2001 | C12N 15/86 |
| WO | WO-2005012536 | A1 | 2/2005 | |
| WO | WO-2005030261 | A1 | 4/2005 | |
| WO | WO-2010/0072900 | | 7/2010 | |
| WO | WO-2010128182 | A1 | 11/2010 | |
| WO | WO-2012000188 | A1 | 1/2012 | |
| WO | WO-2012043710 | A1 | 4/2012 | |
| WO | WO-2014-170389 | | 10/2014 | |

OTHER PUBLICATIONS

Kosai, "Multifactorial growth-regulated adenovirus Prospects for development and commercialization Proprietary technology to innovative medicine from Japan", (2016) 34(1):19-25.

Bilsland et al., (2016). "Virotherapy: cancer gene therapy at last?," F1000 Research., 5:2105, 9 pages.

Bristol et al., (2003). "In Vitro and in Vivo Activities of an Oncolytic Adenoviral Vector Designed to Express GM-CSF", Mol. Ther., 7(6):755-764.

Caruso et al., (1996). "Adenovirus-mediated interleukin-12 gene therapy for metastatic colon carcinoma," Proc Natl Acad Sci USA, 93(21):11302-11306.

Chen et al., (1995). "Combination gene therapy for liver metastasis of colon carcinoma in vivo," Proc Natl Acad Sci USA, 92(7):2577-2581.

Chen et al., (1996). "Combination Suicide and Cytokine Gene Therapy for Hepatic Metastases of Colon Carcinoma: Sustained Antitumor Immunity Prolongs Animal Survival," Cancer Res., 56(16):3758-3762.

Chen et al., (2013). "Oncology meets immunology: the cancer-immunity cycle," Immunity, 39(1) 1-10.

Garver et al., (1994). "Strategy for achieving selective killing of carcinomas," Gene Ther., 1:46-50.

International Search Report and Written Opinion dated Feb. 5, 2019, for PCT Patent Application No. PCT/JP2018/041541 filed on Nov. 8, 2018, 14 pages (2 pages of English translation, 12 pages of Official copy).

Kamizono et al., (2005). "Survivin-responsive conditionally replicating adenovirus exhibits cancer-specific and efficient viral replication," Cancer Res. 65(12): 5284-5291.

Kimura et al., (2004). "Cell cycle-dependent regulation of the human aurora B promoter," Biochem. Biophys. Res. Commun., 316:930-6.

Koshikawa et al., (2000). "Therapeutic Efficacy of the Suicide Gene Driven by the Promoter of Vascular Endothelial Growth Factor Gene against Hypoxic Tumor Cells," Cancer Res., 60(11):2936-2941.

Kumagai et al., (1996). "Eradication of Myc-overexpressing Small Cell Lung Cancer Cells Transfected with Herpes Simplex Virus Thymidine Kinase Gene Containing Myc-Max Response Elements," Cancer Res., 56(2):354-358.

Latham et al., (2000). "Prostate-specific Antigen Promoter/Enhancer Driven Gene Therapy for Prostate Cancer: Construction and Testing of a Tissue-specific Adenovirus Vector," Cancer Res., 60(2)334-341.

Li et al., (1999). "The Cancer Antiapoptosis Mouse Survivin Gene: Characterization of Locus and Transcriptional Requirements of Basal and Cell Cycle-dependent Expression," Cancer Res., 59: 3143-3151.

Li et al., (1999). "Transcriptional analysis of human survivin gene expression," Biochem. J., 344:305-311.

Liu et al., (2003). "ICP34.5 deleted herpes simplex virus with enhanced oncolytic, immune stimulating, and anti-tumour properties," Gene Ther., 10(4):292-303.

Mizuguchi et al., (1999). "A simple method for constructing E1- and E1/E4-deleted recombinant adenoviral vectors," Hum. Gene Ther., 10(12):2103-7.

Morrison et al., (1989). "1,25-dihydroxyvitamin D-responsive element and glucocorticoid repression in the osteocalcin gene," Science, 246:1158-1161.

Nagano et al., (2005). "An efficient construction of conditionally replicating adenoviruses that target tumor cells with multiple factors," Gene Therapy, 12:1385-1393.

Nemunaitis et al., (1020). "A Phase I Study of Telomerase-specific Replication Competent Oncolytic Adenovirus (Telomelysin) for Various Solid Tumors," Molecular Therapy, 18(2):429-434.

Neuman et al., (1994). "Transcription of the E2F-1 gene is rendered cell cycle dependent by E2F DNA-binding sites within its promoter," Mol. Cell. Biol., 14(10):6607-6615.

Pandha et al., (1999). "Genetic prodrug activation therapy for breast cancer: A phase I clinical trial of erbB-2-directed suicide gene expression," J. Clin. Oncol., 17:2180-2189.

Schrewe et al., (1990). "Cloning of the complete gene for carcinoembryonic antigen: analysis of its promoter indicates a region conveying cell type-specific expression," Mol. Cell. Biol., 10(6):2738-2748.

Takakura et al., (1999). "Cloning of Human Telomerase Catalytic Subunit (hTERT) Gene Promoter and Identification of Proximal Core Promoter Sequences Essential for Transcriptional Activation in Immortalized and Cancer Cells," Cancer Res., 59:551-557.

Tanaka et al., (2002). "Cell-cycle-dependent regulation of human aurora A transcription is mediated by periodic repression of E4TF1," J. Biol. Chem., 277(12):10719-26.

Tanoue et al., (2014). "Survivin-responsive conditionally replicating adenovirus kills rhabdomyosarcoma stem cells more efficiently than their progeny," J Trans Med., 12: 27, 13 pages.

Vile et al., (1993). "In Vitro and in Vivo Targeting of Gene Expression to Melanoma Cells," Cancer Res., 53:962-967.

Watanabe et al., (2016). "Oncolytic Adenovirus Expressing Cytokines Enhances Anti- Tumor Efficacy of Mesothelin-Redirected CAR-T Cells", Blood, 128 (22):3360, 3 pages.

(56) References Cited

OTHER PUBLICATIONS

Xie et al., (1999). "Co-expression of vascular endothelial growth factor (VEGF) and its receptors (flk-1 and flt-1) in hormone-induced mammary cancer in the Noble rat," Br. J. Cancer, 81:1335-1343.
Yan et al., (2014). "Combination of E2F-1 promoter-regulated oncolytic adenovirus and cytokine induced killer cells enhances the antitumor effects in an orthotopic rectal cancer model", Tumor Biol., 35:1113-1122.
Zhu et al., (2005). "Linked Tumor-Selective Virus Replication and Transgene Expression from E3-Containing Oncolytic Adenoviruses", J. Virol., 79(9):5455-5465.
Horikawa et al., "Assessment of an altered E1B promoter on the specificity and potency of triple-regulated conditionally replicating adenoviruses: implications for the generation of ideal m-CRAs," Cancer Gene Therapy (2011) 18:724-733.
Supplementary European Search Report for EP 18875645.6, dated Jul. 27, 2021, 12 pages.
Xie et al., "A novel triple-regulated oncolytic adenovirus carrying PDCD5 gene exerts potent antitumor efficacy on common human leukemic cell lines," Apoptosis (2009) 14:1086-1094.

\* cited by examiner

A. HaK/mGM-CSF

B. HaP-T1/mGM-CSF

C. BHK-21/mGM-CSF

D. HaK/hGM-CSF

A. Serum

B. Tumor

C. Spleen

\*, P < 0.05 vs E2Fpr-GM-CSF
, P < 0.05 vs RSVpr-GM-CSF
(Student's *t* test)

Survival analysis after each treatment

SEQUENCE LISTING

```
<160> NUMBER OF SEQ ID NOS: 23

<210> SEQ ID NO 1
<211> LENGTH: 394
<212> TYPE: DNA
<213> ORGANISM: Rous sarcoma virus

<400> SEQUENCE: 1
gcttcgcgat gtacgggcca gatatacgcg tatctgaggg gactagggtg tgtttaggcg      60
aaaagcgggg cttcggttgt acgcggttag gagtcccctc aggatatagt agtttcgctt     120
ttgcataggg aggggaaat gtagtcttat gcaatactct tgtagtcttg caacatggta     180
acgatgagtt agcaacatgc cttacaagga gagaaaaagc accgtgcatg ccgattggtg     240
gaagtaaggt ggtacgatcg tgccttatta ggaaggcaac agacgggtct gacatggatt     300
ggacgaacca ctgaattccg cattgcagag atattgtatt taagtgccta gctcgataca     360
ataaacgcca tttgaccatt caccacattg gtgt                                 394

<210> SEQ ID NO 2
<211> LENGTH: 269
<212> TYPE: DNA
<213> ORGANISM: Homo sapiens

<400> SEQUENCE: 2
ggtaccatcc ggacaaagcc tgcgcgcgcc ccgccccgcc attggccgta ccgcccgcg       60 ccgccgcccc atctcgcccc tcgccgccgg gtccggcgcg ttaaagccaa taggaaccgc     120
cgccgttgtt cccgtcacgg ccggggcagc caattgtggc ggcgctcggc ggctcgtggc     180
tctttcgcgg caaaaaggat ttggcgcgta aaagtggccg ggactttgca ggcagcggcg     240 gccggggcg gagcgggatc gagccctcg                                       269

<210> SEQ ID NO 3
<211> LENGTH: 1310
<212> TYPE: DNA
<213> ORGANISM: Mus musculus
```

<400> SEQUENCE: 3

```
cacctcttac tccacacctg ggattaaaac aaaaacacat tcataaaaca taactgggct    60
tttagagaaa ctcaaattct cactacaggg aagagtccta tctgaaccgg gccatgagag   120
aggagaggaa gagatgagag aggaagagga ccaagagaga tgtggaaagt ttcagaccaa   180
gggagcaagc tgtggaaatg gctggtctat acagggaaga aagctcaaa cgctggactg    240
gtgaggttta ggatagggc agggtgagaa gagctgggg gagccacagg aattgatact     300
tgatccatgt ttcttcggga cgtgacaaaa cccctcttgt tccagctgcc tatgtgctat   360
gatctgttct tcctcacaat ctgtgaggtg gcctggagct cattggaggc ccactggcag   420
gaagcctact gagatttatt gaaaaggaaa ccgaattatc agggcactcg tttgcaacgc   480
caacctgggc tgtgttcggg gcatgcccag catgctgtgt gcagtgtgaa gctctttaga   540
agccactgca accacaggcc gcccgacagg aacagagaca ctgaaaacgg gcccgcagca   600
aggcaggctc agcagccaac agtcacaccc aggaagcagt attttcttc tgctcctgga    660
ctctcttgcg gtgtatggct gattcccttt ggtctgagac aggccgatgg tctcagaaat   720
agacacccat tgactttctt ttccagcgct gggacataca gaccccgcct ccatcccagg   780
gtgtctatag aaggatggc ggctgctgca gggaggaggg tctcctgtct tcctaagggc     840
gcccctccac cagcctgtgg gtgggtccga ggcacttcca ttccgatatc tagctggcca   900
aatcctgcaa accttgaggc aggaagaacc tgcagagcac atgggacttg cagcggacat   960
gctttaaaga ggtgccccag gcccgtccac cgccctcggc caccctccgt gtcctctggg  1020
gagcagctgc ggaagattcg agtcagaata gcaagaagga accgcagcag aaggtacaac  1080
tcccagcatg ccctgcgccc gccacgccca caaggccagg cgcagatggg cgtggggcgg  1140
gactttcccg gctcgcctcg cgccgtccac tcccagaagg cagcgggcga gggcgtgggg  1200
ccggggctct cccggcatgc tctgcggcgc gcctccgccc gcgcgatttg aatcctgcgt  1260
ttgagtcgtc ttggcggagg ttgtggtgac gccatcatgg gagctccggc              1310
```

<210> SEQ ID NO 4
<211> LENGTH: 1495
<212> TYPE: DNA
<213> ORGANISM: Homo sapiens

<400> SEQUENCE: 4

```
aaattgacat cgggccgggc gcagtggctc acatctgtaa tcccagcact ttgggaggcc    60
gaggcaggca gatcacttga ggtcaggagt ttgagaccag cctggcaaac atggtgaaac   120
cccatctcta ctaaaaatac aaaaattagc ctggtgtggt ggtgcatgcc tttaatctca   180
gctactcggg aggctgaggc aggagaatcg cttgaacccg tggcggggag gaggttgcag   240
tgagctgaga tcatgccact gcactccagc ctgggcgata gagcgagact cagtttcaaa   300
taaataaata aacatcaaaa taaaaagtta ctgtattaaa gaatggggc ggggtgggag    360
gggtggggag aggttgcaaa aataaataaa taaataaata aaccccaaaa tgaaaaagac   420
agtggaggca ccaggcctgc gtggggctgg agggctaata aggccaggcc tcttatctct   480
ggccatagaa ccagagaagt gagtggatgt gatgcccagc tccagaagtg actccagaac   540
acctgttcc aaagcagagg acacactgat ttttttttta ataggctgca ggacttactg     600
ttggtgggac gccctgcttt gcgaagggaa aggaggagtt tgccctgagc acaggcccc    660
accctccact gggctttccc cagctcccttt gtcttcttat cacggtagtg gcccagtccc   720
```

| | |
|---|---|
| tggcccctga ctccagaagg tggccctcct ggaaacccag gtcgtgcagt caacgatgta | 780 |
| ctcgccggga cagcgatgtc tgctgcactc catccctccc ctgttcattt gtccttcatg | 840 |
| cccgtctgga gtagatgctt tttgcagagg tggcaccctg taaagctctc ctgtctgact | 900 |
| tttttttttt ttttagactg agttttgctc ttgttgccta ggctgagtg caatggcaca | 960 |
| atctcagctc actgcaccct ctgcctcccg ggttcaagcg attctcctgc ctcagcctcc | 1020 |
| cgagtagttg ggattacagg catgcaccac cacgcccagc taattttgt atttttagta | 1080 |
| gagacaaggt ttcaccgtga tggccaggct ggtcttgaac tccaggactc aagtgatgct | 1140 |
| cctgcctagg cctctcaaag tgttgggatt acaggcgtga ccactgcac ccggcctgca | 1200 |
| cgcgttcttt gaaagcagtc gagggggcgc taggtgtggg cagggacgag ctggcgcggc | 1260 |
| gtcgctgggt gcaccgcgac cacgggcaga gccacgcggc gggaggacta caactcccgg | 1320 |
| cacaccccgc gccgccccgc tctactccc agaaggccgc gggggtgga ccgcctaaga | 1380 |
| gggcgtgcgc tcccgacatg ccccgcggcg cgccattaac cgccagattt gaatcgcggg | 1440 |
| acccgttggc agaggtggcg gcggcggcat gggtgccccg acgttgccccc ctgcc | 1495 |

<210> SEQ ID NO 5
<211> LENGTH: 1840
<212> TYPE: DNA
<213> ORGANISM: Homo sapiens

<400> SEQUENCE: 5

| | |
|---|---|
| tcacatgaga gattagaggc tgacaccacc cagaagatca cctattctgt ctgcataaca | 60 |
| aacttgattc accatacatt tcctccgttc accgtccat aacttgtgtt agagctgctt | 120 |
| cccgccccc gccccaatt tctctattcat tcctttcagt agctcaggat gccatgtagg | 180 |
| ctttaatcat ctgacttcaa cttttagtct cgtattttgt gggactcctg tacgtaatta | 240 |
| aatatcgttt ttctcccatg gacaatgttc agttacccga aaaaaatggg agattcttaa | 300 |
| ggtaccaata aagaatgaaa atcacaagtg gtagtctgg caaagaaaag ttgatgagag | 360 |
| attctactgt taacgttggg ttaatatgac tcgaataatt tccgtatgct agctcaatgc | 420 |
| tttacatgca catcctgttt accctgcagt aatctgttaa ttcgtcttat gtgaatttaa | 480 |
| ctctttgtcc taataaggta cctggaagga tggagggaag ccattttggg ttcccctaca | 540 |
| ccactgttct atccggtctc ttcacttctg ctgagcacat cccgggtgta catatacaca | 600 |
| cacacacaca catatatgtg tgtgtatata tatgtatatg tgtgtgtgtg tatatatata | 660 |
| tatatatatt ttaagtggcc cacccctaac ttctcaactc ccacagaacg ttcactcgcc | 720 |
| aggtaaacag aagcctaatt atccccaatt tgcaggtcag cacacgagga caagaacccg | 780 |
| atccaggacc ggatacatcg cagttggaaa ggctagaaca cagatgcccc ctcactatat | 840 |
| cgccgcgacc atctggatgc agaggcgaac taaggactgg gtgggaatgg aagcgaggcc | 900 |
| cttcgagaag aggaagggt gcaggccagc cgggcaactt aggaaacaca agtagaggc | 960 |
| gcatgccacc ttgctaactc tcgactcttc cagtctcgcc ccagtcgttt ctgtggtttt | 1020 |
| ctctaaatgc cccagccgac cgcaccagct actctccccg tgtcccagca ccagctggtc | 1080 |
| cggttctctt ggtatcccgc tctctcctgg aaaaatggag gcgcgaatcc tgcccaatct | 1140 |
| accgctccga gcgcacgttc actgcgcacg ctgaaagggc gccaagccga ccgctgcgct | 1200 |
| atcgatcggt cccactctct cttgcttttc tcgccatctt acttactggc acgttcaaag | 1260 |
| gttagttcac ctcctcggac tttatctcca atgcgtcaag cttgacgtca aggggctgtt | 1320 |
| gcttcaccga taaatggccg accgcggaga gcaccctggg gctgggactg ccacaggtct | 1380 |

```
ggctggccgt tggctccacc acttccgggt tcttagggag caagtcgcct gcgcgcggtg    1440
tgcgccctta aacgcgactc aaggcgtcgg gtttgttgtc aaccaatcac aaggcagcct    1500
cgctcgagcg caggccaatc ggctttctag ctagagggtt taactcctat ttaaaaagaa    1560
gaacctttga attctaacgg ctgagctcct ggaagacttg ggtccttggg tcgcaggtgg    1620
gagccgacgg gtgggtacac cgtgggggat atctcagtgg cggacgagga cggcggggac    1680
aaggggcggc tggtcggagt ggcggagcgt caagtccctg tcggttcctc cgtccctgag    1740
tgtccttggc gctgccttgt gcccgcccag cgcctttgca tccgctcctg ggcaccgagg    1800
cgccctgtag gatactgctt gttacttatt acagctagag                          1840

<210> SEQ ID NO 6
<211> LENGTH: 478
<212> TYPE: DNA
<213> ORGANISM: Homo sapiens

<400> SEQUENCE: 6
tgggactgcc acaggtctgg ctggccgttg gctccaccac ttccgggttc ttagggagca      60
agtcgcctgc gcgcggtgtg cgcccttaaa cgcgactcaa ggcgtcgggt ttgttgtcaa     120
ccaatcacaa ggcagcctcg ctcgagcgca ggccaatcgg ctttctagct agagggttta    180
actcctattt aaaagaaga accttttgaat tctaacggct gagctcctgg aagacttggg    240
tccttgggtc gcaggtggga gccgacgggt gggtacaccg tgggggatat ctcagtggcg    300
gacgaggacg gcggggacaa ggggcggctg gtcggagtgg cggagcgtca agtccctgtc    360
ggttcctccg tccctgagtg tccttggcgc tgccttgtgc ccgcccagcg cctttgcatc    420
cgctcctggg caccgaggcg ccctgtagga tactgcttgt tacttattac agctagag     478

<210> SEQ ID NO 7
<211> LENGTH: 2140
<212> TYPE: DNA
<213> ORGANISM: Homo sapiens

<400> SEQUENCE: 7
agtagcacta gaagcagcaa tgagggctgc atgcttccct gctcacttcc agaaatctct      60
tcctccatac cttgccctat acatcttttc atctatatca tttgtaatac actttatgat     120
aaaccagtaa acgttaagtg tttccttgag ctgcccagca ttctgagcaa gaaactgatt     180
cccactagct ggcccactta aatcacaggc ttatgcctga tccaataacc ataatctgga     240 ataaaggta ttgattagta taagttaatt ggggctcatt tctggacctg caatgaagtc      300
agtttccttc tcaaatcctc aaaactctaa gtgctttcag aagtgggaat aaagctgggc     360
gcagtggctc acgcctgtaa tccaagcact tgggagacc aaggcgggcg atcacctga      420 ggccagcctg agcaatgtga tgaaaccccg tctctactaa aaatacaaaa attagccggg    480
cgtggtcaca tgcacctata atcctaggta ctcgggaggc tgagacagga gaatcagttg    540
caccctggag gaggaggttg tggtgagctg agattgtgcc attgcactcc agcctgggca    600
acacagcgaa tcttcatctc aaaaaaaaaa aaaaagtga gatttaaata ggtcttcatc     660
aacctaggga tttggggttg tcagcaacag aaactactac agaaaccgac tgcatagact    720
ggagagacag gtggtccct aaaggaaaaa tagagtgtta aagaaaagga aagagtgct      780 ggacagtaca tacttaataa atatccactg gttatttcat agaaggccca aaaatgtatt    840
tatttaaccc agtaatgaaa tctgagggtt aggaagagca gaaagaagg aagtgtggca    900
```

```
ggaaggagga aaaatgaaag tgggcccaaa caacacggca gctaacagag atcttgcaac        960
gaaaggtcta ttggtggaaa aactcctccc aggaatgtca gaacttttaa gaacgacata       1020
gtaatgacac aagaataaac acacaggcaa atgagcaaac aacggaatac aaagtctaga       1080
aatagacaca agtaaatatg ctaacattat atatcaaggg cagcatttaa attctgttgg       1140
ggcagtttgt ttaacaaatg gtgttgacat aactggcgct ccatcgggca gagaagttag       1200
accccagctc atacatgcat aaggataaac tccagttaca ttaaagattt aatttttttt       1260
ataaaaagaa gaaggccggg cacggtggct cacgcctgta atcccagcat ttgggaagc        1320 cgaggcgggt ggatcacctg aggacaggag ttcgagacca gattggccaa cacagcgaaa       1380
acccgtctct aataaaaata caaaaattag ccaggcgtgg tggcgggcgc ttgtaatccc       1440
agctactcgg gtggctgagg cacgagaatc gcttgaaccc gggaggcaga ggttgcagca       1500
agcccagata gcaccattat actccagcct gagcgacaga gagagacctg tctcaaaaaa       1560
ggaaaaaaaa aagaaaaga aaaagcaaga taattcactg ggggaatttg gggaactttt       1620
cctaaactgg aagccaagcg tgagcccttc tcattccgcc tcttccattg ggttcccatg       1680
acttacgtca caggacatcg agccaatggg aactaggcat gggcgacgag cttgcccaat       1740
ggggccgggg cggagattt gaaaagtcct tggccaggc gcggcgtggc agattcagtt        1800
gtttgcgggc ggccgggaga gtagcagtgc cttggacccc aggtgagctg gcctcctgtc       1860
gcaggccttg cgccgggagt gggcagatga tcaggtagat cagagggtcc gttgggctgg       1920
cctgcgcgca cgccgcaggg ctggaaggag gtagggacga tagcagggcg ggggcggtga       1980
gaccagcgcc cagattgggg ctagtgtgct gacctgctcc cttttaccag ctcgggctag       2040
cgcttccggc tcgatcggtc caaccctcc ctctctctct cttttttctct gcttctcacg       2100 gctgtttccc ttctccgccc agctctcctc cccctttctc                             2140

<210> SEQ ID NO 8
<211> LENGTH: 546
<212> TYPE: DNA
<213> ORGANISM: Homo sapiens

<400> SEQUENCE: 8
tcactggggg aatttgggga aacttttccta aactggaagc caagcgtgag cccttctcat        60
tccgcctctt ccattgggtt cccatgactt acgtcacagg acatcgagcc aatgggaact       120
aggcatgggc gacgagcttg cccaatgggg ccggggcggg agatttgaaa agtccttggc       180
cagggcgcgg cgtggcagat tcagttgttt gcggcggcc gggagagtag cagtgccttg        240
gaccccaggt gagctggcct cctgtcgcag gccttgcgcc gggagtgggc agatgatcag       300
gtagatcaga gggtccgttg gctggcctg cgcgcacgcc gcaggctgg aaggaggtag        360 ggacgatagc agggcggggg cggtgagacc agcgcccaga ttggggctag tgtgctgacc       420
tgctcccttt taccagctcg ggctagcgct tccggctcga tcggtccaac ccctccctct       480
ctctctcttt ttctctgctt ctcacggctg ttttccttct ccgcccagct ctcctccccc       540
tttctc                                                                    546

<210> SEQ ID NO 9
<211> LENGTH: 576
<212> TYPE: DNA
<213> ORGANISM: cytomegalovirus
```

<400> SEQUENCE: 9

```
tagtaatcaa ttacggggtc attagttcat agcccatata tggagttccg cgttacataa    60
cttacggtaa atggcccgcc tggctgaccg cccaacgacc cccgcccatt gacgtcaata   120
atgacgtatg ttcccatagt aacgccaata gggactttcc attgacgtca atgggtggag   180
tatttacggt aaactgccca cttggcagta catcaagtgt atcatatgcc aagtacgccc   240
cctattgacg tcaatgacgg taaatggccc gcctggcatt atgcccagta catgacctta   300
tgggactttc ctacttggca gtacatctac gtattagtca tcgctattac catggtgatg   360
cggttttggc agtacatcaa tgggcgtgga tagcggtttg actcacgggg atttccaagt   420
ctccacccca ttgacgtcaa tgggagtttg ttttggcacc aaaatcaacg ggactttcca   480
aaatgtcgta acaactccgc cccattgacg caaatgggcg gtaggcgtgt acggtgggag   540
gtctatataa gcagagctgg tttagtgaac cgtcag                             576
```

<210> SEQ ID NO 10
<211> LENGTH: 38
<212> TYPE: DNA
<213> ORGANISM: Artificial Sequence
<220> FEATURE:
<223> OTHER INFORMATION: primer

<400> SEQUENCE: 10

```
tcagtcctcg agccatgggg taccatccgg acaaagcc                            38
```

<210> SEQ ID NO 11
<211> LENGTH: 44
<212> TYPE: DNA
<213> ORGANISM: Artificial Sequence
<220> FEATURE:
<223> OTHER INFORMATION: primer

<400> SEQUENCE: 11

```
ggacgtaccg gtgtcgacac tagtcgaggg ctcgatcccg ctcc                     44
```

<210> SEQ ID NO 12
<211> LENGTH: 38
<212> TYPE: DNA
<213> ORGANISM: Artificial Sequence
<220> FEATURE:
<223> OTHER INFORMATION: primer

<400> SEQUENCE: 12

```
tcagtcaccg gtaggaggat gtggctgcag aatttact                            38
```

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13

```
ggacgtgggc cctcattttt ggcctggttt tt                                  32
```

<210> SEQ ID NO 14
<211> LENGTH: 38
<212> TYPE: DNA
<213> ORGANISM: Artificial Sequence
<220> FEATURE:
<223> OTHER INFORMATION: primer

<400> SEQUENCE: 14
tcagtcctcg agccatgggc ttcgcgatgt acgggcca          38

<210> SEQ ID NO 15
<211> LENGTH: 44
<212> TYPE: DNA
<213> ORGANISM: Artificial Sequence
<220> FEATURE:
<223> OTHER INFORMATION: primer

<400> SEQUENCE: 15
ggacgtaccg gtgtcgacac tagtacacca atgtggtgaa tggt          44

<210> SEQ ID NO 16
<211> LENGTH: 38
<212> TYPE: DNA
<213> ORGANISM: Artificial Sequence
<220> FEATURE:
<223> OTHER INFORMATION: primer

<400> SEQUENCE: 16
tcagtcaccg gtgccacaat gtacaggatg caactcct          38

<210> SEQ ID NO 17
<211> LENGTH: 32
<212> TYPE: DNA
<213> ORGANISM: Artificial Sequence
<220> FEATURE:
<223> OTHER INFORMATION: primer

<400> SEQUENCE: 17
ggacgtgggc cctcaagtca gtgttgagat ga          32

<210> SEQ ID NO 18
<211> LENGTH: 38
<212> TYPE: DNA
<213> ORGANISM: Artificial Sequence
<220> FEATURE:
<223> OTHER INFORMATION: primer

<400> SEQUENCE: 18
tcagtcaccg gtgcaggcat gtacagcatg cagctcgc          38

<210> SEQ ID NO 19
<211> LENGTH: 32
<212> TYPE: DNA
<213> ORGANISM: Artificial Sequence
<220> FEATURE:
<223> OTHER INFORMATION: primer

<400> SEQUENCE: 19
ggacgtgggc ccttattgag ggcttgttga ga          32

<210> SEQ ID NO 20
<211> LENGTH: 38
<212> TYPE: DNA
<213> ORGANISM: Artificial Sequence
<220> FEATURE:
<223> OTHER INFORMATION: primer

<400> SEQUENCE: 20
tcagtcaccg gttgagtaat gagaatttcg aaaccaca          38

<210> SEQ ID NO 21
<211> LENGTH: 32

```
<212> TYPE: DNA
<213> ORGANISM: Artificial Sequence
<220> FEATURE:
<223> OTHER INFORMATION: primer

<400> SEQUENCE: 21
ggacgtgggc cctcaagaag tgttgatgaa ca                                    32

<210> SEQ ID NO 22
<211> LENGTH: 38
<212> TYPE: DNA
<213> ORGANISM: Artificial Sequence
<220> FEATURE:
<223> OTHER INFORMATION: primer

<400> SEQUENCE: 22
tcagtcaccg gttaagtaat gaaaattttg aaaccata                              38

<210> SEQ ID NO 23
<211> LENGTH: 32
<212> TYPE: DNA
<213> ORGANISM: Artificial Sequence
<220> FEATURE:
<223> OTHER INFORMATION: primer

<400> SEQUENCE: 23
ggacgtgggc cctcaggacg tgttgatgaa ca                                    32
```

ONCOLYTIC VIRUS (ONCOLYTIC IMMUNOTHERAPY) CAPABLE OF EFFECTIVELY TREATING EVEN METASTATIC CANCER WHILE ENSURING SAFETY, WITH EXPRESSION CONTROL SYSTEM PROVIDING OPTIMAL EXPRESSION LEVEL OF MOUNTED IMMUNOGENIC GENE

CROSS REFERENCE TO RELATED APPLICATIONS

This application is a national stage application under 35 U.S.C. § 371 of International Application No. PCT/JP2018/041541, filed internationally on Nov. 8, 2018, which claims benefit of Japanese application Nos. 2017-215579 filed Nov. 8, 2017, and 2018-050722 filed Mar. 19, 2018. The contents of the above patent applications are incorporated by reference herein in their entirety.

SUBMISSION OF SEQUENCE LISTING ON ASCII TEXT FILE

The present application is being filed along with a Sequence Listing in electronic format. The Sequence Listing is provided as a file entitled 165732000300SeqList.TXT, created Aug. 23, 2020, which is 15,680 bytes in size. The information in the electronic format of the Sequence Listing is incorporated by reference in its entirety.

TECHNICAL FIELD

The present invention relates to the field of cancer treatment utilizing an oncolytic virus with an immunity-inducing gene, i.e., oncolytic immunotherapy.

BACKGROUND ART

Oncolytic immunotherapy uses an oncolytic virus, a "genetically recombinant virus that specifically proliferates in cancer cells and exhibits a killing effect on the cells", with an immunity-inducing gene. As the oncolytic immunotherapy, a cytokine gene-carried oncolytic virus (T-Vec from Amgen Inc.) was approved as a first-in-class drug in Europe and the United States at the end of 2015. The oncolytic immunotherapy is expected worldwide as the most promising candidate for an innovative cancer therapeutic drug (Non Patent Literatures 1 to 3).

The inventors led the world in developing-immunogene therapy transferring immune genes by using non-proliferative viral vectors in the 1990s, the early days of gene therapy (Non Patent Literatures 4 to 6). The inventors have then made own research and development over long years, as publishing many articles about immunogene therapy.

Meanwhile, the inventors have modified three factors of a conditionally replicating adenovirus, one of the oncolytic viruses a viral proliferation control part, a therapeutic gene, and viral characteristics, and developed an efficient preparation of "conditionally replicating adenovirus regulated with multiple-tumor specific factors (m-CRA)" as a next generation conditionally replicating adenovirus that ensures safety due to highly controlled viral proliferation specifically in cancer cells by multiple factors, and that can be incorporated a therapeutic gene which enhance a therapeutic effect (Non Patent Literature 7 and Patent Literature 1). Adenovirus, albeit being a middle sized virus having a genome size of 30 to 40 kb, is not easy to genetically recombine. Unlike non-proliferative adenovirus, there even existed no standardized technique of efficiently preparing the conditionally replicating adenovirus. Accordingly, the development of m-CRA highly genetically recombined at a plurality of locations, or studies involving experiments which prepare and compare a plurality of m-CRA candidates for screening were also difficult. Thus, the inventors first developed m-CRA. technology which enables preparation and an exploratorily test for many m-CRA candidates for the first time, and then have developed m-CRA drugs having pharmaceutical characteristics far exceeding other oncolytic viruses in contending technology. At first, the inventors have developed tumor specific promoters in a viral proliferation controlling part which serves as the backbone of m-CRA, such as survivin reactive m-CRA (Surv.m-CRA) whose viral proliferation is controlled by survivin gene promoter also used in the present invention, and Aurora kinase reactive m-CRA (Patent Literature 2) whose viral proliferation is controlled by Aurora kinase gene promoter. Surv.m-CRA has exhibited superiority over contending technologies in both of safety and therapeutic effect being superior to best ever contending technology (CRA whose viral proliferation is controlled by Tert promoter; CRA having the same type of backbone has been reported for favorable results in clinical trials and thus considered to be one of the previous best contending technologies; Non Patent Literature 8) (Non Patent Literature 9). Surv.m-CRA has also exhibited superiority over conventional techniques as being capable of effectively treating cancer stem cells that do not respond to existing treatment techniques (anticancer agents and radiation therapy) (Non Patent Literature 10). Surv.m-CRA "without a therapeutic gene" was designated as Surv.m-CRA-1, which has been confirmed to be safe in nonclinical trials, and is currently under the investigator Initiated Clinical Trials in human cancer patients by the inventors which is confirming favorable results in human. Surv.m-CRA-1 is an oncolytic virus drug for specific (safe) and effective treatment of cancer cells through amplified viral proteins which specifically and highly-efficiently proliferate only within cancer cells.

CITATION LIST

Patent Literature

Patent Literature 1: Japanese Patent No. 4478775
Patent Literature 2: Japanese Patent No. 5963363

Non Patent Literature

Non Patent Literature 1: Bilsland, A E et al. (2016) F1000 Research.; 5:2105.
Non Patent Literature 2: Liu B L et al. (2003) Gene Ther.; 10(4): 292-303.
Non Patent Literature 3: Chen D S et. al. (2013) Immunity.; 39(1): 1-10.
Non Patent Literature 4: Chen S H et al. (1995) Proc Natl Acad Sci USA.; 92(7): 2577-2581.
Non Patent Literature 5: Chen S H et al. (1996) Cancer Res.; 56(16): 3758-3762.
Non Patent Literature 6: Caruso M et al. (1996) Proc Natl Acad Sci USA.; 93(21): 11302-11306.
Non Patent Literature 7: Nagano S, et at. (2005) Gene Ther. 12(18): 1385-1393
Non Patent Literature 8: Nemunaitis J, et al. Mol Ther. 2010 18: 429-34

Non Patent Literature 9: Kamizono J, et al.: Survivin-responsive conditionally replicating adenovirus exhibits cancer-specific and efficient viral replication. Cancer Res. 65(12): 5284-5291, 2005

Non Patent Literature 10: Tanoue K, et al. J Trans Med. 12: 27.doi: 10.1186/1479-5876-12-27, 2014

SUMMARY OF INVENTION

For now, The field of oncolytic immunotherapy has been focused on search for immunity-inducing genes that exert an effective therapeutic effect, but there is no consideration that "whether it is necessary to ensure special safety, due to oncolytic viruses characteristics as 'proliferating only in tumor'". For the first time, the inventors have paid attention to such safety problems which may be caused by an excess production of immunity-inducing factors by oncolytic virus. Unlike a gene therapy utilizing conventional non-prolifera-tive vectors (most of which transfer one gene per cell, or even multiple genes per cell, the transferred number of gene itself does not change after gene transfer), an oncolytic virus "proliferates" in cancer cells and thus amplifies the carried immunity-inducing gene in correlation to the proliferation, and as a result, excess amount of immunity-inducing factors may be produced. In other words, the inventors have found that: for use of an oncolytic immunotherapeutic agent, safety is concerned due to an excess production of immunity-inducing-factors from an immunity-inducing gene carried in a proliferated oncolytic virus; and as a solution thereto, an optimal gene expression level specific to this system exists for the immunity-inducing gene carried in the oncolytic virus; and more specifically, it is necessary for selecting a promoter inducing and/or controlling the optimal expression level of the immunity-inducing gene carried in the oncolytic virus.

The problems thus discovered, which have motivated the present invention, have been gained by the own specialized findings and long years of experience of the inventors, and accumulated as unpublished know-how of the present researchers. Specifically, the present inventions for the medicament (optimal oncolytic immunotherapeutic agent that overcomes the problems mentioned above) and related technologies are invented, based on the own unpublished findings accumulated for long years on immunogene therapy, by analyzing a plurality of Surv.m-CRA-2 candidates mounting an immunity related gene prepared utilizing the unique developed m-CRA preparation technique.

Accordingly, the present invention is based on an unprecedented novel concept for "finding an expression control system for an oncolytic immunotherapeutic agent (oncolytic virus with an immunity-inducing gene), that provides the optimal expression level of a carried immunity-inducing gene in order to induce a strong therapeutic effect even on metastatic cancer while ensuring safety by eliminating adverse reactions". Thus, an object of the present invention is to develop an oncolytic immunotherapy virus having the optimal therapeutic effect while ensuring high safety.

Assuming that an immunity-inducing gene is incorporated into Surv.m-CRA, the inventors have comprehensively compared and studied combinations of various promoters of different strengths and various cytokine genes. As a result, the inventors have found that novel Surv.m-CRA with an immunity-inducing gene whose expression is controlled by cell cycle specific or tumor specific E2F promoter (E2Fp) (hereinafter, also referred to as "this genetically recombinant virus") serves as an oncolytic immunotherapeutic agent having high safety and the optimal therapeutic effect. A plurality of so-called strong constitutive promoters suggested to have ubiquitously strong transcriptional activity have previously been reported. However, detailed difference in characteristics, particularly, detailed difference in expression level among the promoters, is not clear. Particularly, the detailed characteristics of various strong constitutive promoters have not been analyzed. for use in the control of expression of an immunity-inducing gene carried in an oncolytic virus. This our studies have revealed for the first time that "among such promoters, CA promoter (a modified chicken beta-actin promoter with human cytomegalovirus immediate-early enhancer) has very strong promoter activity; RSV promoter (Rous sarcoma virus long terminal repeat), one of the strong constitutive promoters, has stronger activity even being much lower than that of the CA promoter; particularly, the copy number of the oncolytic virus carried gene within cancer cells is remarkably amplified. along with viral proliferation; and for the purpose of controlling the expression of an immunity-inducing gene carried on an oncolytic immunotherapy virus, a promoter having the "optimal (moderate degree of)" transcriptional activity is suitable". In other words, for the purpose of expressing an immunity-inducing gene in an oncolytic virus, use of E2F promoter can drastically improve safety as compared with the expression control by very strong promoters (CA promoter, etc.) or strong promoters (RSV promoter). A promoter of transcription factor E2F (E2Fp) mainly targets a gene encoding cancer suppressor gene product pRB, and performs cell cycle specific or cancer specific expression control. Thereby, the immunity-inducing gene is expressed transiently and only at a low level during the S phase in normal cells other than cancer cells. On the other hand, the "optimal (moderate degree of)" expression control of the immunity-inducing gene is specifically performed in cancer cells, which enables drastically improved safety with a strong therapeutic effect. Surprisingly, it has also been found that the oncolytic virus (oncolytic immunotherapeutic agent) in which the immunity-inducing gene expression is controlled by the E2F promoter can not only drastically improve safety but enhance and maximize the therapeutic effect of the immunity-inducing gene.

Specifically, the inventors have found that Surv.m-CRA/E2Fp-mGM-CSF efficiently infects to and proliferates in hamster derived cancer cells and induces high expression of GM-CSF within the cells, and that, in orthotopic cancer hearing hamster models, the virus exhibits a strong tumor suppressive effect not only on primary tumor to, which the virus were injected but on metastatic foci, without causing lethal adverse reactions. This therapeutic effect may be due to induction of direct cell death by the oncolytic virus, and furthermore, due to very efficient induction of cancer specific systemic antitumor immunity mainly consisted of cell-mediated immunity, which is induced by local generation of various cancer antigens released through specific (safe) and strong killing of cancer cells, and simultaneous sustained secretion of a high concentration of the immunity-inducing factor at the tumor local site, thereby induced antitumor immunity leads death of not only the primary tumor but even cancer in metastatic foci. In the Examples of the present invention for in vivo therapeutic effect, the virus not only significantly increased a tumor disappearance effect on the local tumor to where virus is administered, but was able to achieve drastic blocking of distant metastasis owing to the induction of systemic antitumor immunity by local treatment (this therapeutic agent has large difference and superiority over conventional therapeutic techniques which cannot treat systemic metastatic cancer by local treatment), as compared to Surv.m-CRA-1 without cytokine which is currently under Investigator Initiated Clinical Trials (which has been proved to have therapeutic effect human patients who did not respond to standard treatments). Therefore, early clinical application of the invention is largely expected for drastic improvement in safety and an innovatively strong therapeutic effect on cancer.

Specifically, the present invention relates to a genetically recombinant virus having an immunity-inducing gene operably linked to E2F promoter (E2Fp). More preferably, the present invention relates to a conditionally replicating virus with multiple-tumor specific factors (oncolytic virus). Specifically, the present invention relates to the following aspects:

(1) An oncolytic virus comprising an immunity-inducing gene operably linked to the downstream of E2F promoter (E2Fp) or a promoter having activity equivalent thereto.
(2) The oncolytic virus of (1), wherein the promoter having activity equivalent to E2F promoter (E2Fp) is survivin promoter, Aurora kinase A gene promoter, or Aurora kinase B gene promoter.
(3) The oncolytic virus of (1), wherein the promoter is E2F promoter (E2Fp) or survivin promoter.
(4) The oncolytic virus of (1), wherein the promoter is E2F promoter (E2Fp).
(5) The oncolytic virus of any one of (1) to (4), wherein the immunity-inducing gene is cytokine gene.
(6) The oncolytic virus of (5), wherein the cytokine gene is a gene of any one cytokine selected from a group consisting of Activin A, ANGPTL5, BAFF, BD-2(β-Defensin-2), BD-3(β-Defensin-3), BDNF, BMP-2, BMP-4, BMP-6, BMP-7, BMP-10, CCL1, CCL2(MCP-1), CCL3 (MIP-1α), CCL4(MIP-1β), CCL5(RANTES), CCL6, CCL7(MCP-3), CCL8(MCP-2), CCL9(MIP-1γ), CCL11 (Eotaxin-1), CCL12(MCP-5), CCL13(MCP-4), CCL14, CCL15(MIP-1δ), CCL16, CCL17(TARC), CCL18 (PARC), CCL19(MIP-3β), CCL20(MIP-3α), CCL21 (Exodus-2), CCL22, CCL23, CCL24(Eotaxin-2), CCL25 (TECK), CCL26(MIP-4α), CCL27, CCL28, CO40-Ligand (TRAP), CD137(4-1BB)-Ligand, CNTF, CT-1, CX3CL1(Fractalkine), CXCL1(GRO1), CXCL2(MIP-2α, GRO2) CXCL3(MIP-2β, GRO3), CXCL4(PF4), CXCL5, CXCL6, CXCL7, CXCL9, CXCL10, CXCL11, CXCL12(SDF-1α), CXCL13, CXCL14, CXCL15, CXCL16, CXCL17, DKK-1, DLL1, EGFs, EG-VEGF (Prokineticin 1), FasL, FGF-1(acidic FGF), FGF-2(basic FGF), FGF-3, FGF-4(HGBF-4), FGF-5, FGF-6, FGF-7 (KGF, HBGF-7), FGF-8, FGF-9(HBGF-9), FGF-10 (KGF-2), FGF-11, FGF-12, FGF-13, FGF-14, FGF-16, FGF-17, FGF-18, FGF-19, FGF-20, FGF-21, FGF-22, FGF-23, Flt3-Ligand, Galectin-1, Galectin-3, G-CSF, GDF-11, GDNF, GM-CSF, HB-EGF, HGF, IFN-α2a, IFN-α2b, IFN-β1a, IFN-β1b, IFN-γ1b, IGF-1, IGF-2, IL-1α, IL-1β, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, LIF, M-CSF, MIF, NGF-β, Noggin, NT-3(NTF-3), NT-4(NTF-4), Oncostatin M, OPG(TNFRSF11B), PDGF-AA, PDGF-AB, PDGF-BB, Pleiotrophin, Prolactin (Mammotropin), RANKL, R-Spondin-1, R-Spondin-2, R-Spondin-3, SCF (c-kit Ligand), SHH (C24II), TGF-α, TGF-β1, TGF-β3, TNF-α, TNF-β, TPO (MDGF), TRAIL, TSLP, VEGF, XCL1, and XCL2.
(7) The oncolytic virus of (6), wherein the cytokine gene is GM-CSF.
(8) The oncolytic virus of any one of (1) to (7), wherein at least one promoter for nucleic acids encoding an element essential for viral replication or assembly is replaced with a promoter for an organ specific highly expressed factor or with a promoter for a cancer cell specific highly expressed factor.
(9) The oncolytic virus of (8), wherein the promoter for an organ specific highly expressed factor is selected from a group consisting of an albumin promoter, α-fetoprotein promoter, prostate specific antigen (PSA) promoter, mitochondrial creatine kinase (MCK) promoter, myelin basic protein (MB) promoter, glial fibrillary acidic protein (GFAP) promoter, and neuron-specific enolase (NSE) promoter.
(10) The oncolytic virus of (8), wherein the promoter for a cancer cell specific highly expressed factor is selected from a telomerase reverse transcriptase (TERT) promoter, carcinoembryonic antigen (CEA) promoter, hypoxia responsive element (HRE) promoter, Grp78 promoter, L-Plastin promoter, hexokinase II promoter, survivin promoter, and Aurora kinase promoter.
(11) The oncolytic virus of (10), wherein the promoter for the cancer cell specific highly expressed factor is survivin promoter, human Aurora kinase A promoter, or human Aurora kinase B promoter.
(12) The oncolytic virus of (10), wherein the promoter for the cancer cell specific highly expressed factor is survivin promoter.
(13) The oncolytic virus of any one of (1) to (12), which is adenovirus.
(14) The oncolytic virus of (13), wherein the at least one element essential for viral replication or assembly is selected from E1A, E1AΔ24, E1B and E1BΔ55K.
(15) The oncolytic virus of (13), wherein the at least one element essential for viral replication or assembly is E1A.
(16) The oncolytic virus of any one of (1) to (15), which further comprises an expression cassette including nucleic acids encoding cell a toxic factor or a therapeutic factor operably linked to an exogeneous promoter.
(17) A therapeutic agent for cancer, comprising the oncolytic virus of any one of (1) to (16).

Advantageous Effects of Invention

The virus of the present invention can achieve a high anticancer effect, without causing any adverse reaction, by controlling the expression of an immunity-inducing gene by employing a promoter having moderate strength promoter activity.

DESCRIPTION OF EMBODIMENTS

Figure 1:
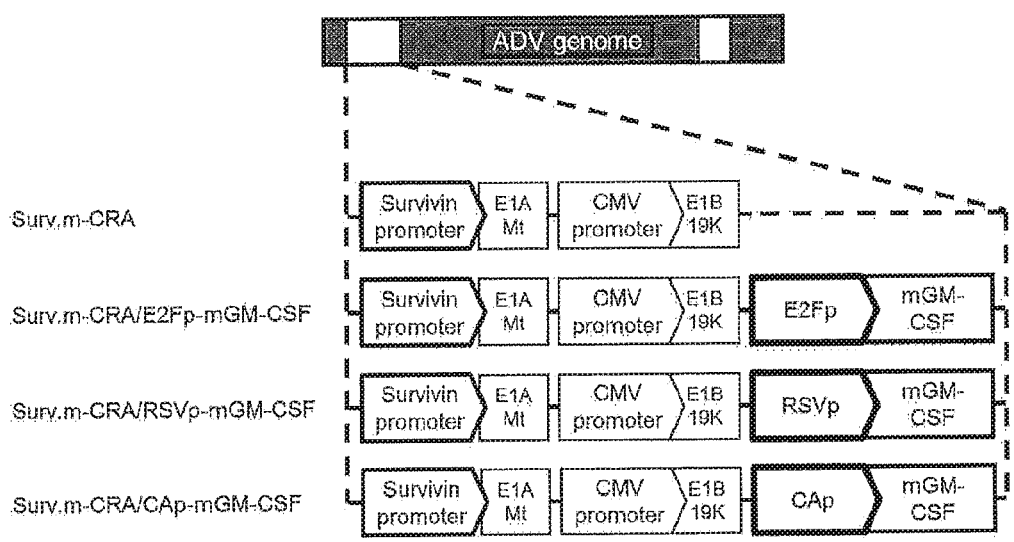
FIG. 1 is a schematic view of GM-CSF expression Surv.m-CRA having an insert of an expression cassette of mouse GM-CSF cDNA linked to each promoter (E2F promoter, RSV promoter, and CA promoter) in Surv.m-CRA containing survivin promoter incorporated upstream of E1A, an early gene essential for adenovirus proliferation.

A feature of the present virus is that an immunity-inducing gene carried on an oncolytic virus is operably linked to E2F promoter or a promoter having activity equivalent thereto, whereby the virus exhibits a strong tumor suppressive effect without causing any lethal adverse reaction.

The "immunity-inducing gene" is not particularly limited as long as the gene encodes a protein having an activity of stimulating immunity or a functional peptide fragment thereof. A cytokine gene or its functional peptide fragment gene is preferred, such as Activin A, ANGPTL5, BAFF, BD-2(β-Defensin-2), BD-3(β-Defensin-3), BDNF, BMP-2, BMP-4, BMP-6, BMP-7, BMP-10, CCL1, CCL2(MCP-1), CCL3(MIP-1α), CCL4(MIP-1β), CCL5(RANTES), CCL6, CCL7(MCP-3), CCL8(MCP-2), CCL9(MIP-1γ), CCL11 (Eotaxin-1), CCL12(MCP-5), CCL13(MCP-4), CCL14, CCL15(MIP-1δ), CCL16, CCL17(TARC), CCL18(PARC), CCL19(MIP-3β), CCL20(MIP-3α), CCL21(Exodus-2), CCL22, CCL23, CCL24(Eotaxin-2), CCL25(TECK), CCL26(MIP-4α), CCL27, CCL28, CO40-Ligand (TRAP), CD137(4-1BB)-Ligand, CNTF, CT-1, CX3CL1(Fractalkine), CXCL1(GRO1), CXCL2(MIP-2α, GRO2), CXCL3(MIP-2β, GRO3), CXCL4(PF4), CXCL5, CXCL6, CXCL7, CXCL9, CXCL10, CXCL11, CXCL12(SDF-1α), CXCL13, CXCL14, CXCL15, CXCL16, CXCL17, DKK-1, DLL1, EGFs, EG-VEGF (Prokineticin 1), FasL, FGF-1 (acidic FGF), FGF-2(basic FGF), FGF-3, FGF-4(HGBF-4), FGF-5, FGF-6, FGF-7(KGF, HBGF-7), FGF-8, FGF-9 (HBGF-9), FGF-10(KGF-2), FGF-11, FGF-12, FGF-13, FGF-14, FGF-16, FGF-17, FGF-18, FGF-19, FGF-20, FGF-21, FGF-22, FGF-23, Flt3-Ligand, Galectin-1, Galectin-3, G-CSF, GDF-11, GDNF, GM-CSF, HB-EGF, HGF, IFN-α2a, IFN-α2b, IFN-β1a, IFN-β1b, IFN-γ1b, IGF-1, IGF-2, IL-1α, IL-1β, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, LIF, M-CSF, MIF, NGF-β, Noggin, NT-3(NTF-3), NT-4(NTF-4), Oncostatin M, OPG (TNFRSF11B), PDGF-AA, PDG E-AB, PDGF-BB, Pleiotrophin, Prolactin (Mammotropin), RANKL, R-Spondin-1, R-Spondin-2, R-Spondin-3, SCF (c-kit Ligand), SHH (C24II), TGF-α, TGF-β1, TGF-β3, TNF-α, TNF-β, TPO (MDGF), TRAIL, TSLP, VEGF, XCL1, and XCL2.

The "E2F promoter" is a promoter region of E2F gene, which is a main target of a representative cancer suppressor gene product pRB. Examples of the E2F promoter include the sequence of SEQ ID NO: 2. The E2F promoter need not to have the full length sequence of SEQ ID NO: 2, and may have a portion of the sequence of SEQ ID NO: 2 as long as the object of the present invention can be attained.

The promoter having activity equivalent to E2F promoter is not particularly limited as long as the promoter has promoter activity equivalent to the E2F promoter within tumor cells. Examples thereof include survivin promoter, Aurora kinase A gene promoter, and Aurora kinase B gene promoter.

Promoters of mouse and human survivin genes have been isolated, and sequence information thereon has been disclosed (see e.g., Li, F. and Altieri, D. C., Cancer Res., 59: 3143-3151, 1999; and Li, F. and Altieri, D. C., Biochem. J., 344: 305-311, 1999). The survivin promoter used in the present virus is a promoter of human survivin gene or its ortholog gene of any of other mammals (e.g., monkeys, cattle, horses, pigs, dogs, cats, sheep, goats, rabbits, mice, and rats), preferably a promoter of human or mouse derived survivin gene, more preferably a promoter of human survivin gene.

The nucleotide sequence length of the survivin promoter is not particularly limited as long as the promoter is capable of activating the transcription of the downstream-linked gene specifically in target cancer cells and to an extent that sufficient therapeutic activity is exerted against the cancer cells. For example, mouse survivin gene promoter comprising a nucleotide sequence from −173 to −19 with a translation initiation site defined as +1 (nucleotide sequence from positions 1124 to 1278 in the nucleotide sequence of SEQ ID NO: 3), and human survivin gene promoter comprising a nucleotide sequence from −173 to −1 with a translation initiation site defined as +1 (nucleotide sequence from positions 1296 to 1468 in the nucleotide sequence of SEQ ID NO: 4) are capable of obtaining the specificity and transcriptional activity of interest. Thus, preferably, the survivin promoter used in this genetically recombinant virus comprises at least a nucleotide sequence from positions 1124 to 1278 in the nucleotide sequence of SEQ ID NO: 3, or at least a nucleotide sequence from positions 1296 to 1468 in the nucleotide sequence of SEQ ID NO: 4. The upper limit of the nucleotide sequence length of the survivin promoter is not particularly limited. However, too long a 5' upstream site may rather have an unfavorable effect on the transcriptional activity or specificity of the promoter. For example, human survivin gene promoter having a nucleotide sequence from approximately −6000 to −1 with a translation initiation site defined as +1 is capable of obtaining the specificity and transcriptional activity of interest. Preferably, the 5' end of the promoter is positioned downstream of −3000, more preferably downstream of −1500. In using survivin promoters derived from other mammals, suitable sequence length ranges of the promoters can be determined by preparing vectors for a reporter gene linked to varying lengths of promoters, transferring the vectors to cancer cells, and evaluating the promoter activity with the expression of the reporter as an index.

The survivin promoter can be prepared by cloning genomic DNA including the survivin promoter region from genomic DNA extracted from cells or tissues derived from human or any of other mammals (e.g., monkeys, cattle, horses, pigs, dogs, cats, sheep, goats, rabbits, mice, and rats) using the nucleic acid of a known survivin gene promoter sequence (see e.g., Li, F. and Altieri, D. C., Cancer Res., 59: 3143-3151, 1999; and Li, F. and Altieri, D. C., Biochem. J., 344: 305-311, 1999) as a probe, cleaving the genomic DNA into DNA fragments including a desired partial promoter sequence with DNase, for example, an appropriate restriction enzyme, separating by gel electrophoresis, then recovering a desired band, and purifying the DNA. Alternatively, a partial sequence of the survivin promoter may be amplified and isolated by PCR using primers synthesized based on the known survivin gene promoter sequence with a crude liquid extract of the cells or genomic DNA isolated therefrom as a template. For mammals having an unknown nucleotide sequence of the survivin promoter, the nucleotide sequences of the survivin promoter regions of the animals can be obtained by BLAST search on the genomic DNA of the animals with the survivin cDNA sequences of the animals as a query. Also, the survivin promoter can be obtained by chemically synthesizing a nucleic acid including the whole or a portion of the nucleotide sequence of the survivin promoter based on the known survivin gene promoter sequence (e.g., the nucleotide sequence of SEQ ID NO: 3 or SEQ ID NO: 4) using a commercially available automatic DNA/RNA synthesis apparatus.

Promoters of human Aurora kinase A gene and Aurora kinase B gene have already been reported (Tanaka, M. et al., J. Biol. Chem., 277 (12): 10719-26, 2002; and Kimura, M. et al., Biochem. Biophys. Res. Commun., 316: 930-6, 2004). The Aurora kinase promoter is not particularly limited as long as the promoter is derived from a gene belonging to the Aurora kinase family. Examples thereof include mammalian (e.g., humans, monkeys, cattle, horses, pigs, dogs, cats, sheep, goats, rabbits, mice, and rats) orthologs of drosophila Aurora-A, -B and -C genes. The Aurora kinase promoter is preferably a promoter of Aurora kinase A gene or Aurora kinase B gene derived from a human or any of other mammals, more preferably a promoter of human Aurora kinase A gene or Aurora kinase B gene.

The nucleotide sequence length of the Aurora kinase promoter is not particularly limited as long as the promoter is capable of activating the transcription of the downstream-linked gene in a manner specific for target disease cells (e.g., cancer cells) and to an extent that sufficient therapeutic activity is exerted against the disease of interest. For example, human Aurora kinase A gene promoter comprising a nucleotide sequence from −124 to +354 with a translation initiation site defined as +1 (nucleotide sequence of SEQ ID NO: 6; nucleotide sequence from positions 1363 to 1840 in the nucleotide sequence of SEQ ID NO: 5) is capable of obtaining the specificity and transcriptional activity of interest. The Aurora kinase A gene promoter herein encompasses not only full length Aurora kinase A gene promoter but a promoter comprising the nucleotide sequence of SEQ ID NO: 6. Human Aurora kinase B gene promoter comprising a nucleotide sequence from −185 to +361 with a translation initiation site defined as +1 (nucleotide sequence of SEQ ID NO: 8; nucleotide sequence from positions 1595 to 2140 in the nucleotide sequence of SEQ ID NO: 7) is capable of obtaining the specificity and transcriptional activity of interest. The Aurora kinase B gene promoter herein encompasses not only full length Aurora kinase B gene promoter but a promoter comprising the nucleotide sequence of SEQ ID NO: 8. Preferably, the Aurora kinase promoter comprises at least a nucleotide sequence from positions 1363 to 1840 in the nucleotide sequence of SEQ ID NO: 5, or at least a nucleotide sequence from positions 1595 to 2140 in the nucleotide sequence of SEQ ID NO: 7. The upper limit of the nucleotide sequence length of the Aurora kinase promoter is not particularly limited. However, too long a 5' upstream site may rather have an unfavorable effect on the transcriptional activity or specificity of the promoter. For example, human Aurora kinase A gene promoter having a nucleotide sequence from −1486 to +354 with a translation initiation site defined as +1 (nucleotide sequence of SEQ ID NO: 5), or human Aurora kinase B gene promoter having a nucleotide sequence from −1779 to +361 with a translation initiation site defined as +1 (nucleotide sequence of SEQ ID NO: 7) is capable of obtaining the specificity and. transcriptional activity of interest. Thus, in a preferred embodiment, the 5' terminal nucleic acid of the Aurora kinase promoter used in the vector of the present invention is any one of the 1st to 1363rd nucleotides in the nucleotide sequence of SEQ ID NO: 5, or any one of the 1st to 1595th nucleotides in the nucleotide sequence of SEQ ID NO: 7. In using Aurora kinase promoters derived from other mammals, a preferred region can be selected in the same way as above.

The Aurora kinase promoter can be prepared by cloning genomic DNA including the Aurora kinase promoter region from genomic DNA extracted from cells or tissues derived from human or any of other mammals (e.g., monkeys, cattle, horses, pigs, dogs, cats, sheep, goats, rabbits, mice, and rats) using the nucleic acid of a known Aurora kinase gene promoter sequence (see e.g., Tanaka, M. et al., J. Biol. Chem., 277 (12): 10719-26, 2002; and Kimura, M. et al., Biochem. Biophys. Res. Commun., 316: 930-6, 2004) as a probe, cleaving the genomic DNA into DNA fragments including a desired partial promoter sequence with DNase, for example, an appropriate restriction enzyme, separating by gel electrophoresis, then recovering a desired band, and purifying the DNA. Alternatively, a partial sequence of the Aurora kinase promoter may be amplified and isolated by PCR using primers synthesized based on the known Aurora kinase gene promoter sequence with a crude liquid extract of the cells or genomic DNA isolated therefrom as a template. For mammals having an unknown nucleotide sequence of the Aurora kinase promoter, the nucleotide sequences of the Aurora kinase promoter regions of the animals can be obtained by BLAST search on the genomic DNA of the animals with the Aurora kinase cDNA sequences of the animals as a query.

The immunity-inducing gene can be isolated as cDNA by a method known per se from cells or tissues producing the gene, and operably linked to the downstream of E2F promoter or a promoter having activity equivalent thereto. An expression cassette can include a nucleic acid encoding the immunity-inducing gene placed under the control of such a promoter, and preferably can include an appropriate polyadenylation sequence downstream of the nucleic acid or the gene. As mentioned later, a nucleic acid encoding a protein necessary for viral replication or assembly may be placed under the control of a promoter for an organ specific highly expressed factor or of a promoter for a cancer cell specific highly expressed factor in the genetically recombinant virus comprising an immunity-inducing gene operably linked to an E2F promoter or a promoter having activity equivalent thereto. The genetically recombinant virus comprising an. immunity-inducing gene operably linked to an E2F promoter or a promoter having activity equivalent thereto may be deficient in a region that is essential for inducing a cellular environment necessary for viral proliferation in normal cells, but is not necessary for viral proliferation in cancer cells, among regions for viral proteins. The genetically recombinant virus comprising an immunity-inducing gene operably linked to an E2F promoter or a promoter having activity equivalent thereto, may have a nucleic acid encoding a protein necessary for viral replication or assembly which is operably linked to a promoter for an organ specific highly expressed factor or to a promoter for a cancer cell specific highly expressed factor, and may be deficient in a region that is essential for inducing a cellular environment necessary for viral proliferation in normal cells, but is not necessary for viral proliferation in cancer cells.

The term "operably linked" herein means that the promoter is bound such that the promoter enables the expression of a downstream gene in exerting its activity.

In one embodiment, the genetically recombinant virus of the present invention is an oncolytic virus, in other words, conditionally replicating virus (CRV), in which at least one promoter of the oncolytic virus for nucleic acids encoding an element essential for viral replication or assembly is replaced with a promoter for an organ specific highly expressed factor or with a promoter for a cancer cell specific highly expressed factor. A proliferation of this genetically recombinant virus is promoted specifically (more dominantly than in normal cells) in target disease cells providing higher activity to the promoter, such as cancer cells, whereby the cell specific cytotoxic activity and the cell specific expression of another genes incorporated in the viral gene are achieved. In other words, the vector of the present invention is characterized in its proliferation. Further, this genetically recombinant virus can bring a therapeutic effect not only by viral proliferation specific in infected target cells which lead to death (lysis) of the cells, but by repeating the infection and killing of neighboring yet-infected target cells by daughter viruses released from the lysed cells. These process eventually introduce the genetically recombinant virus into many target cancer cells located in a primary tumor to which the virus are injected. The cancer cells are specifically (safely) and strongly killed to reduce the tumor volume. Moreover, the cell death generates various cancer antigens at a tumor local site, and thus simultaneous sustained secretion of the immunity-inducing factor at a high concentration at the tumor local site can much efficiently lead cancer specific systemic antitumor immunity which is mainly consisted of cell-mediated immunity. This induced antitumor immunity can effectively treat not only not-gene transferred cancer cells in the primary tumor but even cancer cells in distant metastatic foci to which no virus given.

The "element essential for viral replication or assembly" means a gene encoding any protein essential for the virus to self-replicate, such as a structural protein of the virus, or a gene encoding any protein essential for the virus to assemble. The element essential for viral replication or assembly differs depending on the viral species used. Examples thereof for adenovirus include E1A, E1B, E2 and E4 which are early genes working to transcriptionally control viral proteins after the start of transcription from the initial stage of infection as well as Rb binding region deficient E1A (E1AΔ24) and p53 binding region deficient E1B (E1BΔ55K) mentioned later. Particularly, E1A is first transcribed after infection with adenovirus, and subsequent viral replication does not occur without the expression of E1A. Therefore, this gene is very suitable for specifically controlling viral proliferation in target cancer cells or the like. Similar effects can be obtained by controlling other early genes essential for viral replication. Late genes encoding structural genes of adenovirus, such as L1, L2, L3, L4 and L5, are transcribed, at the late stage where cell division occurs after infection, into proteins constituting the viral structure. The control of expression of these late genes can also specifically control viral proliferation in target cancer cells or the like. The conditionally replicating virus can be obtained by replacing the endogenous promoter of the gene encoding a protein necessary for viral replication or assembly with a promoter for an organ specific highly expressed factor or with a promoter for a cancer cell specific highly expressed factor.

Examples of the "promoter for an organ specific highly expressed factor" (organ specific promoter) can include promoters for albumin and α-fetoprotein specific for the liver, etc., promoters for prostate specific antigen (PSA) specific for the prostate, promoters for mitochondrial creatine kinase (MCK) specific for various organs such as muscles and the brain, and promoters for myelin basic protein (MB), glia fibrillary acidic protein (GFAP) and neuron specific enolase (NSE) specific for the nervous system of the brain, etc.

Examples of the "promoter for a cancer cell specific highly expressed factor" (cancer cell specific promoter) can include promoters for factors specifically expressed only in cancer cells, i.e., CEA (carcinoembryonic antigen) promoter (Mol. Cell. Biol., 10 (6), 2738-2748, 1990), E2F promoter (Neuman, E. et al., Mol. Cell. Biol., 14 (10), 6607-6615, 1994), and OC (osteocalcin) promoter (Morrison, N. A. et al., Science, 246, 1158-1161, 1989), FLK-1 promoter specific for malignant melanoma, fibrosarcoma, etc. (Xie, B. et al., Br. J. Cancer, 81, 1335-1343, 1999), VEGF promoter specific for lung cancer, etc. (Koshikawa, N. et al., Cancer Res., 60, 2936-2941, 2000), c-Myc promoter specific for small cell lung cancer, etc. (Kumagai, T. et al., Cancer Res., 354-358, 1996), SLPI promoter specific for lung cancer, ovarian cancer, etc. (Garver, R. I. et al., Gene Ther., 1, 46-50, 1994), PSA promoter specific for prostate cancer, etc. (Latham, J. P. et al., Cancer Res., 60, 334-342, 2000), tyrosinase promoter specific for malignant melanoma, etc. Vile, R. G. et al., Cancer Res., 53, 962-967, 1993), AP-2 promoter specific for breast cancer (Pandha, H. S. et al., J. Clin. Oncol., 17, 2180-2189, 1999), telomerase reverse transcriptase (TERT) promoter specific for many cancers including brain tumor (Takakura, M. et al., Cancer Res., 59, 551-557, 1999), and hypoxia responsive element (HRE) promoter, Grp78 promoter, L-Plastin promoter, hexokinase II promoter, and survivin promoter specific for various cancers.

Each promoter carried by the present vector can also be obtained by chemically synthesizing a nucleic acid including the whole or a portion of the nucleotide sequence of the promoter based on a known promoter sequence using a commercially available automatic DNA/RNA synthesis apparatus.

Provided that at least one nucleic acid encoding a protein necessary for viral replication or assembly is placed under the control of the promoter for an organ specific highly expressed or of the promoter for a cancer cell specific highly expressed factor, the viral proliferation or assembly is limited by an environment where the promoter is activated. Therefore, other nucleic acids encoding a protein necessary for viral replication or assembly can be placed under the control of an arbitrary exogenous promoter. In using, for example, a promoter capable of causing constant expression in mammals as the exogenous promoter, a constitutive promoter can be used such as cytomegalovirus (CMV) derived promoter (e.g., CMV immediate early promoter), human immunodeficiency virus (HIV) derived promoter (e.g., HIV LTR), Rous sarcoma virus (RSV) derived promoter (e.g., RSV LTR), mouse mammary tumor virus (MMTV) derived promoter (e.g., MMTV LTR), Moloney mouse leukemia virus (MoMLV) derived promoter (e.g., MoMLV LTR), herpes simplex virus (HSV) derived promoter (e.g., HSV thymidine kinase (TK) promoter), SV40 derived promoter (e.g., SV40 early promoter), Epstein-Barr virus (EBV) derived promoter, adeno-associated virus (AAV) derived promoter (e.g., AAV p5 promoter), adenovirus (AdV) derived promoter (Ad2 or Ad5 tumor late promoter), and gene promoters for mammalian constitutive proteins, such as β-actin gene promoter, PGK gene promoter, and transferrin gene promoter.

Alternatively, an inducible promoter may be used as the arbitrary exogenous promoter. For example, metallothionein-1 gene promoter can be used as such an inducible promoter. In using the metallothionein-1 gene promoter, the expression of viral proteins can be specifically induced in target disease cells at an arbitrary time by locally administering an inducing substance (e.g., heavy metals such as gold, zinc, and cadmium, steroids such as dexamethasone, alkylating agents, chelating agents, and cytokines) to the position of the target disease cells at the desired time.

Alternatively, two or more genes encoding a protein necessary for viral replication or assembly may be placed under the control of the same promoter or different promoters selected from a promoter for a organ specific highly expressed factor and a promoter for a cancer cell specific highly expressed factor.

This genetically recombinant virus may be deficient in a region that is essential for inducing a cellular environment necessary for viral proliferation in normal cells, but is not necessary for viral proliferation in cancer cells, among regions contained in viral proteins. For example, for adenovirus proliferation within normal cells, it is necessary to inactivate Rb and p53 for cell cycle progression. Since the cell cycle has already progressed in cancer cells, the Rb binding region of E1A and the p53 binding region of E1B are not essential for adenovirus proliferation within cancer cells. Accordingly, adenovirus proliferates in cancer cells but does not proliferate in normal cells, i.e., is capable of cancer cell specific viral proliferation, by deleting the 24 KDa region of E1A (E1AΔ24), deleting the 55 KDa region of E1B (E1BΔ55K), or deleting the 19 KDa region of E1B (E1BΔ19). These types of genetically recombinant virus can cause cancer cell specific proliferation even if genes encoding a protein necessary for viral replication are not placed under the control of a cancer cell specific promoter. In the genetically recombinant virus of the present invention, such genes encoding a protein necessary for viral replication or assembly may not be placed under the control of a tissue specific promoter or a cancer cell specific promoter, and this genetically recombinant virus may be deficient in at least one region that is essential for inducing a cellular environment necessary for viral proliferation within normal cells, but is not necessary for viral proliferation within cancer cells (e.g., the 24 KDa region of E1A, the 55 K a region of E1B, and the 19 KDa region of E1B).

Particularly, a genetically recombinant virus in which a gene deficient in such a region that is essential for inducing a cellular environment necessary for viral proliferation in normal cells, but is not necessary for viral proliferation in cancer cells is operably linked to an organ specific promoter or a cancer cell specific promoter is called conditionally replicating virus regulated with multiple factors (m-CRV) (Japanese Patent Laid-Open No. 2005-046101 and International Publication No. WO 2005/012536). Preferably, the present invention provides such a conditionally replicating virus regulated with multiple factors.

The conditionally replicating virus regulated with multiple factors can be prepared as follows: for example, plasmid vector P1 comprising E1A gene (which may be deficient in the 24 KDa region) operably linked to a tissue specific promoter or a cancer specific promoter, and E1B gene (which may be deficient in the 19 KDa or 55 KDa region) operably linked to a constitutive promoter (CMV promoter, etc.), plasmid vector P2 comprising an immunity-inducing gene operably linked to any one type of promoter selected from RSV promoter and E2F promoter, and promoters having activity equivalent thereto, and backbone plasmid P3 comprising the adenovirus genome (which may have a target cell specific mutation within fiber gene) deficient in E1 region, are provided, and these three plasmids are appropriately fused in combination using the Cre recombinase/LoxP system. The plasmid of interest can be selected by utilizing drug resistance gene and on carried in each plasmid to prepare a conditionally replicating adenovirus (CRA) vector plasmid with tissue specific promoter or cancer specific promoter-E1A expression cassette, constitutive promoter-E1B expression cassette, and promoter (any one type of promoter selected from RSV promoter and E2F promoter, and promoters having activity equivalent thereto)-immunity-inducing gene expression cassette. Subsequently, the CRA vector can be prepared by transfecting a cell line complementing E1A (e.g. 293 cells) with the vector.

This genetically recombinant virus may further contain a replication origin for autonomous amplification in host cells and a selective marker gene for the selection of transformed cells (genes conferring resistance to drugs such as tetracycline, ampicillin, kanamycin, hygromycin, and phosphinothricin, genes complementing an auxotrophic mutation, etc.).

The diseases for which this genetically recombinant virus may be used as a vector for treatment is cancer. Examples of the "cancer" herein include, but are not limited to, renal cell carcinoma, fibrosarcoma, myxosarcoma, liposarcoma, chondrosarcoma, osteosarcoma, chordoma, angiosarcoma, endothelial sarcoma, lymphangiosarcoma, endothelial lymphangiosarcoma, synovioma, mesothelioma, Ewing's tumor, leiomyosarcoma, rhabdomyosarcoma, colon cancer, pancreatic cancer, breast cancer, ovarian cancer, prostate cancer, squamous cell carcinoma, basal cell carcinoma, adenocarcinoma, syringocarcinoma, sebaceous adenocarcinoma, papillocarcinoma, papillary adenocarcinoma, cystadenocarcinoma, medullary carcinoma, bronchogenic carcinoma, liver cancer, bile duct cancer, choriocarcinoma, seminoma, embryonal carcinoma, Wilms' tumor, cervical cancer, testicle tumor, lung cancer, small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia, acute myelogenous leukemia, chronic leukemia, polycythemia vera, lymphoma, and multiple myeloma.

The "oncolytic virus" means a genetically recombinant virus that proliferates within infected tumor cells and lyses the infected cells to extracellularly release daughter viruses. As a result, the oncolytic virus kills the infected tumor cells while the daughter viruses infect neighboring uninfected tumor cells and kill the cells. A feature of the oncolytic virus is high tumor cell killing efficiency ascribable to the repetition of this process. The oncolytic virus usually does not cause cytolysis in normal cells. Various methods have already been known in the art by utilizing such a tumor selective cytolysis mechanism. Examples of the genetically recombinant virus used as the oncolytic virus can include adenovirus, retrovirus, adeno-associated virus, herpes virus, herpes simplex virus, lentivirus, vaccinia virus, poxvirus, polio virus, Sindbis virus, and Sendai virus. The adenovirus has advantages such as very high gene transfer efficiency, the capability of being transferred even to non-dividing cells, and very rare integration of transgenes into the host chromosomes.

In one embodiment, this genetically recombinant virus may comprise nucleic acids encoding cell toxic factor or therapeutic factor operably linked to an organ specific promoter or a cancer specific promoter. The nucleic acids encoding cell toxic factor can encode, for example, a protein or RNA that directly or indirectly kills cells or at least inhibits cell growth when the nucleic acids are transcribed (and translated). The nucleic acids encoding therapeutic factor may encode a protein (or RNA) that directly or indirectly brings about a therapeutic effect on a target disease through action other than cell toxic action when the genes are transcribed (and translated). Examples of the nucleic acids encoding cell toxic factor or therapeutic factor include tumor suppressor gene (e.g., p53 and p21 genes), cytokine gene (e.g., GM-CSF, IL-2, IL-4, and IFN genes), apoptosis inducing gene (e.g., Fas), genes encoding constitutive proteins of an ion channel (sodium channel, etc.), genes encoding proteins capable of damaging cells by converting prodrugs into toxic agents (suicide gene) (e.g., HSV-thymidine kinase and cytosine deaminase genes), antisense nucleic acids against causative gene of cancer (e.g., antisense nucleic acids against TGF-β and antisense nucleic acids against survivin), angiostatic gene (e.g., platelet factor IV, angiostatin, endostatin, and soluble VEGF receptor genes), miRNA having cancer suppressive action or mimics thereof, antisense nucleic acids against miRNA having cancer promoting action, aptamers, and ribozymes. The proliferation of the genetically recombinant virus may be sufficiently controlled by adopting the already mentioned promoter and/or gene controlling viral proliferation. Namely, the genetically recombinant virus may rarely proliferate in normal cells and sufficiently proliferate in cancer cells. In such a case, the nucleic. acids encoding cell toxic factor or therapeutic factor mentioned above may be operably linked to the arbitrary exogeneous promoter mentioned above.

The nucleic acids encoding cell toxic factor or therapeutic factor can be isolated as cDNA by a method known per se from cells or tissues producing the nucleic acids, and operably linked to the downstream of Aurora kinase promoter. An expression cassette including the nucleic acids encoding cell toxic factor or therapeutic factor, placed under the control of Aurora kinase promoter preferably includes an appropriate polyadenylation sequence downstream of the nucleic acid or the gene.

Depending on the mammal to be treated, a promoter from the same species thereas is preferably used. However, a promoter from a different species therefrom may be used as long as the promoter is capable of exerting activity that provides sufficient infection efficiency and killing effect. For example, a mouse gene promoter can be used. for a vector for human treatment.

The term "specific" for cancer cells herein is not limited by the case where no activity is exhibited in normal cells, and also encompasses the case where gene expression is driven in normal cells in a therapeutically acceptable range.

This genetically recombinant virus can specifically proliferate in target cancer cells, specifically exert cytotoxicity to the cells, and express the immunity-inducing gene at the optimal expression level. Therefore, this genetically recombinant virus can be used as a therapeutic drug for cancer with alleviated cytokine dependent adverse reactions, after being mixed, if necessary, with a pharmacologically acceptable carrier and prepared into various pharmaceutical formulations such as injectables. In this context, various organic or inorganic carrier substances routinely used as pharmaceutical materials can be used as the pharmacologically acceptable carrier, and are blended, for example, as an excipient, a lubricant, a binder and a disintegrant in a solid preparation or as a solvent, a solubilizing agent, a suspending agent, a tonicity agent, a buffer agent and a soothing agent in a liquid preparation. Pharmaceutical additives such as an antiseptic, an antioxidant, a colorant and a sweeting agent may also be used, if required.

In one aspect, the present invention relates to a method for treating cancer with less damage to non-targeted cells, comprising administration of this genetically recombinant virus to tumor cells. In the method for treating cancer using this genetically recombinant virus, the immunity-inducing protein expressed from the immunity-inducing gene transferred by this genetically recombinant virus is rapidly cleared from serum and spleen related directly to systemic adverse reactions. Hence, this method is advantageous for reducing adverse reactions ascribable to the systemic circulation of excess proteins from the immunity-inducing gene. Thus, this genetically recombinant virus exhibits an equivalent or higher tumor suppressive (tumor cell killing) effect in vivo as compared with a virus for treatment that expresses the immunity-inducing gene in a large amount under the control of a very strongly active promoter such as CA promoter, though the immunity-inducing protein expressed from the immunity-inducing gene transferred by this genetically recombinant virus disappears in a short time. Surprisingly, in the determination of the final and most important therapeutic effect, i.e., prolonged survival rates, this genetically recombinant virus rather produces a stronger therapeutic effect than that of a virus for treatment that brings about a large amount of the immunity-inducing protein through the expression of the immunity-inducing gene in a large amount under the control of a very strongly active promoter such as CA promoter. Specifically, this genetically recombinant virus intratumorally produces a high concentration of the immunity-inducing protein only for a short time, i.e., only for a period necessary for inducing antitumor immunity. The immunity-inducing protein at such a transiently high concentration only at a local site of tumor, i.e., in the optimum. amount for the optimum period, efficiently induces systemic antitumor immunity specific for tumor. As a result, this genetically recombinant virus is sufficiently effective for suppressing tumor growth by inducing the cell death of the tumor cells. Thus, the present invention has showed for the first time that: the immunity-inducing protein at a transiently high concentration only at a local site of tumor, i.e., in the optimum amount for the optimum period can efficiently induce systemic specific (safe) antitumor immunity through a very safe and sufficient therapeutic effect of suppressing tumor growth and treatment at the local site of tumor, and can completely block and/or treat even metastasis to an untreated site; and this immunity-inducing protein is very effective for the final therapeutic effect, i.e., prolonged survival rates. Accordingly, the method for treating cancer, comprising administration of this genetically recombinant virus to a patient, specifically damages or kills tumor cells with low toxicity or damage to non-targeted cells (particularly, normal cells), because the amount of the immunity-inducing protein which is unnecessary for organs or tissues other than tumor and brings about adverse reactions is low and/or because the final product immunity-inducing protein expressed from the immunity-inducing gene disappears in a short period. As one example, the present invention provides a method for treating cancer with an oncolytic virus expressing an immunity-inducing gene, comprising administration of this genetically recombinant virus to tumor cells, wherein the amount of the immunity-inducing protein in spleen or serum, a representative organ or tissue in which the induction of adverse reactions of the immunity-inducing protein and a risk thereof are clearly suggested, is lower and sustained for a shorter time (supplied in the optimum amount for the optimum period) than that of a subject administered with another oncolytic virus having the immunity-inducing gene operably linked to the downstream of CA promoter or RSV promoter. In other words, the present invention may provide a method for treating cancer with an oncolytic virus expressing an immunity-inducing gene, comprising administration of this genetically recombinant virus to tumor cells, wherein the amount of unnecessary circulation and/or supply of the protein expressed from the immunity-inducing gene to the whole body including spleen or serum is drastically lower and sustained for a shorter time (i.e., the therapeutic effect is not decreased and is rather enhanced, and the possibility of adverse reactions is very low) than that of a subject administered with another oncolytic virus having the immunity-inducing gene operably linked to the downstream of RSV promoter.

The therapeutic agent for disease containing this genetically recombinant virus is administrated either by an ex vivo method in which own appropriate cells of the animal to be treated (or the cells from an allogeneic or heterologous animal to the animal to be treated) are taken out of the body, cultured, transfected, and then returned (or transplanted) into the body, or by an in vivo method in which the vector is administered directly into the body of the recipient for transfection. The in vivo method is preferred. In the in vivo method, the preparation can be administrated via injection, a catheter, a balloon catheter, local injection, or the like. Examples of the administration location include administration into blood, intratumoral administration, intraperitoneal administration, and intramuscular administration. Intratumoral administration is preferred.

The dose of the therapeutic agent for disease containing this genetically recombinant virus differs depending on the type of the genetically recombinant virus, promoter activity in target cells, the type of the therapeutic factor, an administration route, the severity of the disease, the animal species of the recipient, the drug receptivity of the recipient, body weight, age, etc. In using, for example, conditionally replicating adenovirus, as the genetically recombinant virus, $1 \times 10^{10}$ to $10^{12}$ particles/tumor of the virus particles can serve as a guideline for administration, because conventional clinical trials for cancer gene therapy confirmed safety at this dose (Molecular Therapy, 18: 429-434, 2010). In actuality, the inventor is now conducting investigator initiated clinical study on Surv.m-CRA-1 (without therapeutic gene) in an amount of $10^{10}$ to $10^{12}$ particles/tumor, and has so far confirmed a therapeutic effect and safety in all cases.

EXAMPLES

Hereinafter, the present invention will be described more specifically with reference to Examples. However, the present invention is not limited by these Examples. All literatures cited herein are incorporated herein by reference in their entirety. The present application claims the priority based on Japanese Patent Application No. 2017-215579 filed on November 8, 2017 and Japanese Patent Application No. 2018-050722 filed on Mar. 19, 2018. These patent applications on which the priority claimed by the present application is based are incorporated herein by reference in their entirety.

(Example 1) Structure of GM-CSF Expression Surv.m-CRA

An expression cassette of mouse GM-CSF cDNA linked to each promoter (E2F promoter, RSV promoter, and CA promoter) was inserted into Surv.m-CRA containing survivin promoter incorporated upstream of E1A, an early gene essential for adenovirus proliferation, to construct three types of GM-CSF expression Surv.m-CRA given below (FIG. 1). The construction of the adenovirus was performed based on the method described in Nagano et al., Gene Therapy (2005) 12, 1385-1393.

(1) Preparation of P1+3 Plasmid

At the first stage of preparation, P1+3 was prepared from proliferation control plasmid P1 and adenovirus backbone plasmids P3 (pAd.HM4 and pAd.HM10; Mizuguchi and Kay, Hum. Gene Ther. 1999) by restriction enzyme treatment.

In the adenovirus backbone plasmid P3, human adenovirus type 5 genomic DNA is carried, while an E1 gene region necessary for viral proliferation is deleted. A proliferation control cassette of approximately 3 kb (Survpr-E1A-CMVpr-E1B19K) prepared from the proliferation control plasmid P1 (pHM5-Survpr-E1A-CMVpr-E1B19K) using I-CeuI and PI-SceI was inserted to the deleted E1 region. This proliferation control cassette structurally has viral proliferation factor E1A and E1B genes linked to downstream of cancer specific survivin promoter and constitutive CMV promoter, respectively. The obtained P1+3 plasmids were designated as pAd.HM4-Survpr-E1A-CMVpr-E1B19K and pAd.HM10-Survpr-E1A-CMVpr-E1B19K, respectively.

(2) Preparation of P2 Plasmid

At the second stage of preparation, mouse GM-CSF cDNA was linked as a therapeutic gene to downstream of each of three promoters (CA promoter, E2F promoter, and RSV promoter) to prepare therapeutic gene transfer plasmids P2.

(2)-1: pUni/CApr-mGM-CSF

In the order of preparation, the CA promoter was first inserted to plasmid pUni/V5-HisC-tet(c) (hereinafter, referred to as pUni) having a LoxP sequence and a BGH poly A sequence. Then, the coding sequence (CDS) of mGM-CSF was further inserted as a therapeutic gene to downstream thereof.

First, the vector pUni was cleaved with StuI (Blunt end) and dephosphorylated in order to prevent self-ligation. The insert CA promoter was excised as a CA promoter sequence followed by a SmaI site by the cleavage of 5' BglII and 3' BamHI from pHM-CAGpr-mKate2, and then blunt-ended. These were ligated to prepare pUni/CApr.

Next, SmaI (Blunt end) positioned downstream of the CA promoter was cleaved from pUni/CApr, and the resulting vector was dephosphorylated in order to prevent self-ligation. Meanwhile, the insert mGM-CSF CDS was excised by the cleavage of 5' EcoRI and 3' BamHI from plasmid pBluescript SKII+mGM-CSF (RDB01469; RIKEN, Japan), and the obtained mGM-CSF CDS was blunt-ended. These were ligated to prepare pUni/CApr-mGM-CSF.

(2)-2: pUni/E2Fpr-mGM-CSF

An E2F promoter sequence was amplified by PCR using pABS4-E2Fp-GFP including the E2F promoter sequence as a template, a sense primer with XhoI and NcoI sites added on the 5' side; 5'-TCAGTCCTCGAGCCATGGGGTAC-CATCCGGACAAAGCC-3' (SEQ ID NO: 10), and an antisense primer with AgeI, SalI and SpeI sites added on the 3' side;
5'-GGACGTACCGGTGTCGACACTAGTCGAGGGCTC-GATCCCGCTCC-3' (SEQ ID NO: 11). After subsequent cleavage with XhoI and AgeI, the resulting sequence was inserted to between the XhoI and AgeI sites of pUni to prepare pUni/E2Fpr. Meanwhile, a mGM-CSF cDNA sequence was amplified by PCR using pBluescript SKII+ mGM-CSF as a template, a sense primer with an AgeI site added on the 5' side; 5'-TCAGTCACCGGTAGGAG-GATGTGGCTGCAGAATTTACT-3' (SEQ ID NO: 12), and an antisense primer with an ApaI site added on the 3' side; 5'-GGACGTGGGCCCTCATTTTTGGCCTGGTTTTT-3' (SEQ ID NO: 13). After subsequent cleavage with AgeI and StuI, the resulting sequence was inserted to between the AgeI and StuI sites of pUni/E2Fpr to prepare pUni/E2Fpr-mGM-CSF.

(2)-3: pUni/RSVpr-mGM-CSF

A RSV promoter sequence was amplified by PCR using pGEM-RSV-S including the RSV promoter sequence as a template, a sense primer with XhoI and NcoI sites added on the 5' side; 5'-TCAGTCCTCGAGCCATGGGCTTCGC-GATGTACGGGCCA-3' (SEQ ID NO: 14), and an antisense primer with AgeI, SalI and SpeI sites added on the 3' side; 5'-GGACGTACCGGTGTCGACACTAGTACAC-CAATGTGGTGAATGGT-3' (SEQ ID NO: 15). After subsequent cleavage with XhoI and AgeI, the resulting sequence was inserted to between the XhoI and AgeI sites of pUni to prepare pUni/RSVpr. Meanwhile, a mGM-CSF cDNA sequence was amplified by PCR using pBluescript SKII+mGM-CSF as a template, a sense primer with an AgeI site added on the 5' side; 5'-TCAGTCACCGGTAGGAG-GATGTGGCTGCAGAATTTACT-3' (SEQ ID NO: 12), and an antisense primer with an ApaI site added on the 3' side; 5'-GACGTGGGCCCTCATTTTTGGCCTGGTTTTT-3' (SEQ ID NO: 13). After subsequent cleavage with AgeI and StuI, the resulting sequence was inserted to between the AgeI and StuI sites of pUni/RSVpr to prepare pUni/RSVpr-mGM-CSF.

(3) Preparation of P1+2+3 Plasmid

At the final stage, P1+2+3 plasmids were prepared from the P1+3 plasmid and the P2 plasmid shown above by the homologous recombination between particular sequences (LoxP) using sequence specific recombinase Cre. First, the P1+3 plasmid (pAd.HM4-Surv.m-CRA) and the P2 plasmid (pUni/CApr-mGM-CSF) were subjected at a molar ratio of 1:0.3 to Cre/LoxP homologous recombination to prepare P1+2+3 plasmid (pAd.HM4-Surv.m-CRA/CApr-mGM-CSF). Likewise, the P1+3 plasmid (pAd.HM10.Surv.m-CRA) and pUni/E2Fpr-mGM-CSF or pUni/RSVpr-mGM-CSF) were subjected at a molar ratio of 1:0.3 to Cre/LoxP homologous recombination to prepare P1+2+3 plasmids (pAd.HM10-Surv.m-CRA/E2Fpr-mGM-CSF and pAd.HM10-Surv.m-CRA/RSVpr-mGM-CSF).

(4) Preparation of Adenovirus

The plasmids pAd.Surv.E1A-CMV.E1B19K, pAd.HM4-Surv.m-CRA/CApr-mGM-CSF, pAd.HM10-Surv.m-CRA/E2Fpr-mGM-CSF and pAd.HM10-Surv.m-CRA/RSVpr-mGM-CSF were each cleaved with restriction enzyme PacI. Then, HEK293 cells, adenovirus producing cells, were transfected with each of the resulting plasmides. Then, virus plaques were isolated and used as seed viruses.

(5) Amplification of Adenovirus

HEK293 cells inoculated to a 24-well plate were infected with each seed virus. The cells and the culture solution were recovered when a cytopathic effect (CPE) of 90% was observed. These virally infected cell suspensions were subjected to three repetitive freezing-thawing operations. Then, HEK293 cells inoculated to a 10 cm dish were infected therewith. Such viral infection and recovery operations were gradually scaled up and amplified into forty 15 cm dishes. These cells and culture solutions were recovered and cryopreserved.

(6) Purification of Adenovirus

Each adenovirus was purified from the recovered cell fluids by cesium chloride density gradient ultracentrifugation. First, a virus band was recovered by primary purification using ultracentrifugation at 35,000 rpm at 10° C. for 1 hour. Then, a virus band was recovered by secondary purification using ultracentrifugation at 35,000 rpm at 10° C. for 18 hours. The recovered virus fluids were fractionated using Econo-pac 10DG desalting column (Bio-Rad Laboratories, Inc.) to obtain purified adenovirus fluids. Then, the number of virus particles was roughly calculated from $OD_{260}$. Then, glycerol was added thereto at a final concentration of 10%, and the mixtures were cryopreserved.

(7) Preparation of IL-2 or IL-15 Expression Surv.m-CRA (7-1) Preparation of Human IL-2 Expression Surv.m-CRA First, human IL-2 cDNA was linked to downstream of E2F promoter to prepare therapeutic gene transfer plasmid P2 (pUni/E2Fpr-hIL-2). In this operation, a hIL-2 cDNA sequence was amplified by PCR using pBluescript SKII+ hIL-2 as a template, a sense primer with an AgeI site added on the 5' side; 5'-TCAGTCACCGGTGCCACAATGTA-CAGGATGCAACTCCT-3' (SEQ ID NO: 16), and an antisense primer with an ApaI site added on the 3' side; 5'-GGACGTGGGCCCTCAAGTCAGTGTTGAGATGA-3' (SEQ ID NO: 17). After subsequent cleavage with AgeI and StuI, the resulting sequence was inserted to between the AgeI and StuI sites of pUni/E2Fpr to prepare pUni/E2Fpr-hIL-2. Then, P1+2+3 plasmid (pAd.HM4-Surv.m-CRA/E2Fpr-hIL-2) was prepared.

(7-2) Preparation of Mouse IL-2 Expression Surv.m-CRA

First, mouse IL-2 cDNA was linked to downstream of E2F promoter to prepare therapeutic gene transfer plasmid P2 (pUni/E2Fpr-mIL-2). In this operation, a mIL-2 cDNA sequence was amplified by PCR using pBluescript SKII+ mIL-2 as a template, a sense primer with an AgeI site added on the 5' side; 5'-TCAGTCACCGGTGCAGGCATGTA-CAGCATGCAGCTCGC-3' (SEG ID NO: 18), and an antisense primer with an ApaI site added on the 3' side; 5'-GGACGTGGGCCCTTATTGAGGGCTTGTTGAGA-3' (SEQ ID NO: 19). After subsequent cleavage with AgeI and StuI, the resulting sequence was inserted to between the AgeI and StuI sites of pUni/E2Fpr to prepare pUni/E2Fpr-mIL-2. Then, P1+2+3 plasmid (pAd.HM4-Surv.m-CRA/E2Fpr-mIL-2) was prepared.

(7-3) Preparation of Human IL-15 Expression Surv.m-CRA

First, human IL-15 cDNA was linked to downstream of E2F promoter to prepare therapeutic gene transfer plasmid P2 (pUni/E2Fpr-hIL-15). In this operation, a hIL-15 cDNA sequence was amplified by PCR using hIL-15 cDNA as a template, a sense primer with an AgeI site added on the 5' side; 5'-TCAGTCACCGGTTGAGTAATGAGAAT-TTCGAAACCACA-3' (SEQ ID NO: 20), aid an antisense primer with an ApaI site added on the 3' side; 5'-GGACGTGGGCCCTCAAGAAGTGTTGATGAACA-3' (SEQ ID NO: 21). After subsequent cleavage with AgeI and StuI, the resulting sequence was inserted to between the AgeI and StuI sites of pUni/E2Fpr to prepare pUni/E2Fpr-hIL-15. Then, P1+2+3 plasmid (pAd.HM4-Surv.m-CRA/E2Fpr-hIL-15) was prepared.

(7-4) Preparation of Mouse IL-15 Expression Surv.m-CRA

First, mouse IL-15 cDNA was linked to downstream of E2F promoter to prepare therapeutic gene transfer plasmid P2 (pUni/E2Fpr-mIL-15). In this operation, a mIL-15 cDNA sequence was amplified by PCR using mIL-15 cDNA as a template, a sense primer with an AgeI site added on the 5' side; 5'-TCAGTCACCGGTTAAGTAATGAAAATTTT-GAAACCATA-3' (SEQ ID NO: 22), and an antisense primer with an ApaI site added on the 3' side; 5'-GGACGTGGGCCCTCAGGACGTGTTGATGAACA-3' (SEQ ID NO: 23). After subsequent cleavage with AgeI and StuI, the resulting sequence was inserted to between the AgeI and StuI sites of pUni/E2Fpr to prepare pUni/E2Fpr-mIL-15. Then, P1+2+3 plasmid (pAd.HM4-Surv.m-CRA/E2Fpr-mIL-15) was prepared.

Then, each adenovirus was prepared, amplified, and purified in the same way as above. Finally, DNA derived from each adenovirus was prepared and then subjected to PCR using each specific primer to confirm specific amplification. Among viruses whose titer was able to be determined, Surv.m-CRA/E2Fpr-mL-2 had $1.5 \times 10^{10}$ PFU/mL, and Surv.m-CRA/E2Fpr-hIL-15 had $2.8 \times 10^{10}$ PFU/mL.

(Example 2) Infection Efficiency of Adenovirus in Hamster Derived Cell

Each adenovirus was studied for its infection efficiency in hamster derived cancer cells (HaK and HaP-T1) and normal cells (BHK-21).

Syrian hamster kidney tumor derived HaK cells were kindly provided by Prof. M. Wold from Saint Louis University School of Medicine. The cells were cultured in DMEM (Dulbecco's Modified Eagle Medium; Nacalai Tesque, Inc.) containing 10% Fetal Bovine Serum (FBS; Biowest SAS) and 1% penicillin-streptomycin (Nacalai Tesque, Inc.) under conditions of 37° C. and 5% $CO_2$. Syrian hamster pancreatic tumor derived HaP-T1 cells were purchased from BRC cell bank of RIKEN, Japan (RBRC-RCB0411). The cells were cultured in MEM (Minimum Essential Medium; Sigma-Aldrich Co. LLC) containing 10% FBS, 1% non-essential amino acids (NEAA; Sigma-Aldrich Co. LLC), 1 mM Sodium Pyruvate (Thermo Fisher Scientific Inc.), and 1% penicillin-streptomycin under conditions of 37° C. and 5% $CO_2$. Syrian hamster baby kidney derived BHK-21 cells were purchased from JCRB cell bank of National Institutes of Biomedical Innovation, Health and Nutrition (JCRB9020). The cells were cultured in MEM containing 10% FBS, 1% NEAA, and 1% penicillin-streptomycin (Nacalai Tesque, Inc.) under conditions of 37° C. and 5% $CO_2$.

The cells of each line inoculated to a 12-well plate on the day before infection were counted on the day of infection and were consequently HaK: $6.45 \times 10^5$ cells/well, HaP-T1: $6.75 \times 10^5$ cells/well, and BHK-21: $6.7.5 \times 10^5$ cells/well. Then, the cells were infected with non-proliferative adenovirus (Ad.CMV-EGFP) expressing ECFP under the control of constitutive and strong CMV (cytomegalovirus) promoter under conditions involving a multiplicity of infection (MOI) of 0, 0.1, 0.3, 1, 3, 10, 30, 100, 300, and 1000 for 1 hour (MOI of 0 represents a virally non-infected control). Then, the cells were cultured for 48 hours and photographed under a fluorescence microscope at the magnification shown in the drawings. Then, the cells were detached from the plate using a trypsin/EDTA solution and analyzed by flow cytometry (FACS) with flow cytometer SH800Z (Sony Corp.) to study an EGFP positive rate (adenoviral gene transduction efficiency) under each condition.

Figure 2A:
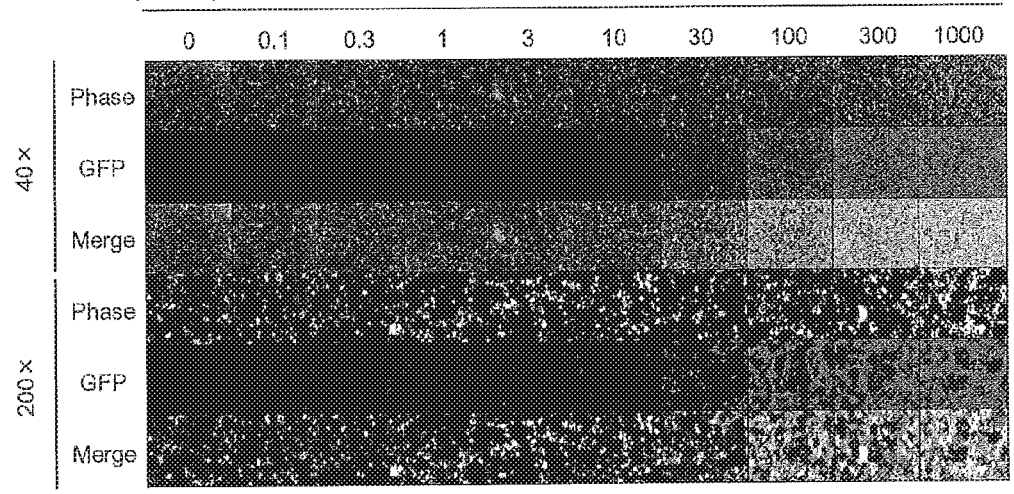
FIG. 2A is a photograph showing the expression of EGFP 48 hours after infection of hamster derived cancer cells (HaK) with control Ad.CMV-EGFP ("non"-proliferative adenovirus incorporating therein a gene construct expressing EGFP under CMV promoter instead of a deleted E1 region) at MOI of 0.1 to 1000.
Figure 2B:
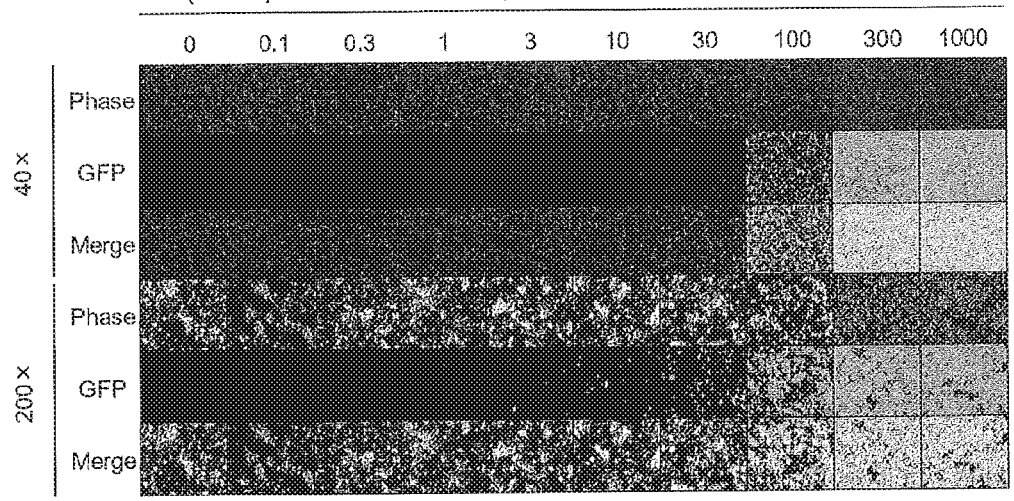
FIG. 2B is a photograph showing the expression of EGFP 48 hours after infection of hamster derived cancer cells (HaP-T1) with control Ad.CMV-EGFP ("non"-proliferative adenovirus incorporating therein a gene construct expressing EGFP under CMV promoter instead of a deleted E1 region) at MOI of 0.1 to 1000.
Figure 2C:
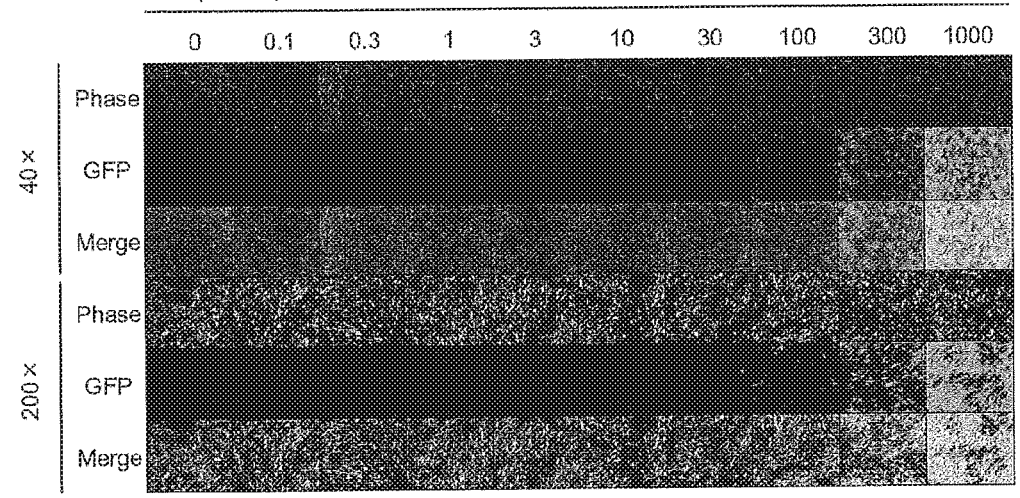
FIG. 2C is a photograph showing the expression of EGFP 48 hours after infection of hamster derived normal cells (BHK-21) with control Ad.CMV-EGFP ("non"-proliferative adenovirus incorporating therein a gene construct expressing EGFP under CMV promoter instead of a deleted E1 region) at MOI of 0.1 to 1000.
Figure 3:
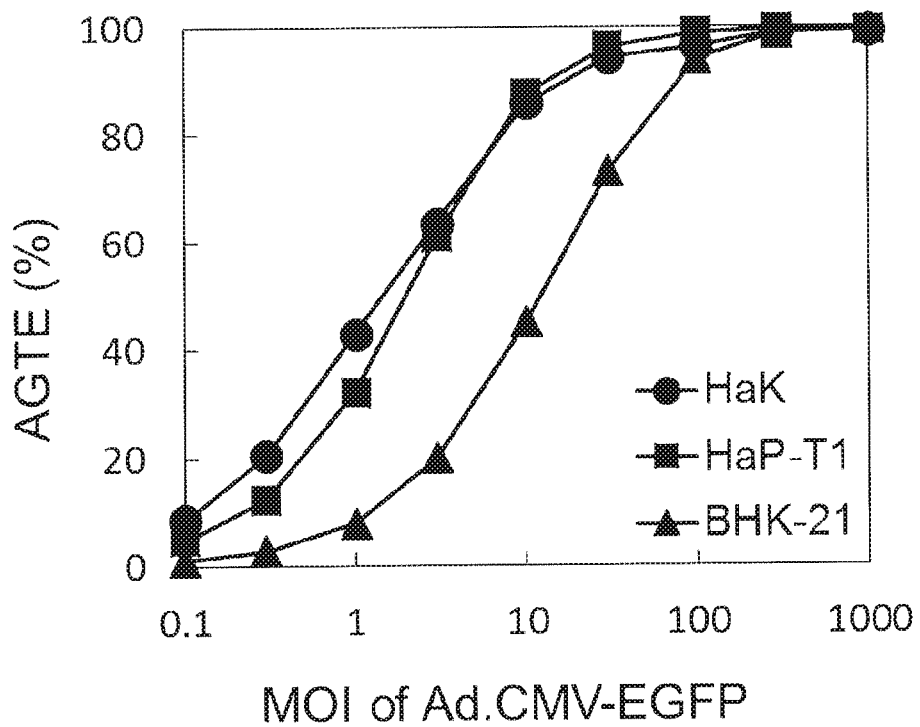
FIG. 3 is a graph showing the expression of EGFP at each MOI of FIG. 2. The ordinate depicts adenoviral gene transduction efficiency (AGTE), and the abscissa depicts MOI (multiplicity of infection) of the viral infection.

As a result, MOI dependent elevation in EGFP positive rate was observed (FIGS. 2 and 3). The adenoviral gene transduction efficiency (AGTE) at MOI of 30 was 95% or more for HaK and HaP-T1 and 70% or more for BHK-21, showing efficient adenovirus infection in all the cells. On the other hand, at MOI of 300 or higher, a strong cytotoxic effect was observed in all the cells.

(Example 3) Promoter Activity in Hamster Derived Cell

E2F, RSV and survivin promoters were studied for their activity in hamster derived cancer cells (HaK and HaP-T1) and normal cells (BHK-21). The cells of each line inoculated to a 6-well plate on the day before infection were counted on the day of infection and were consequently HaK: $1.29 \times 10^6$ cells/well, HaP-T1: $1.0 \times 10^6$ cells/well, and BHK-21: $1.7 \times 10^6$ cells/well. Then, the cells were infected with Ad.dE1.3 deficient in genes E1 and E3 important for viral proliferation (control), or Ad.E2Fp-LacZ, Ad.RSVp-LacZ, or Ad.Survp-LacZ expressing β-galactosidase gene (LacZ) under the control of each promoter at MOI of 30 for 1 hour, and then cultured for 48 hours. Then, β-galactosidase activity in the cell lysates was studied using Beta-Glo® Assay System (Promega Corp.). The experiment was conducted in 3 wells per condition, and the data was indicated by mean±standard deviation.

Figure 4:
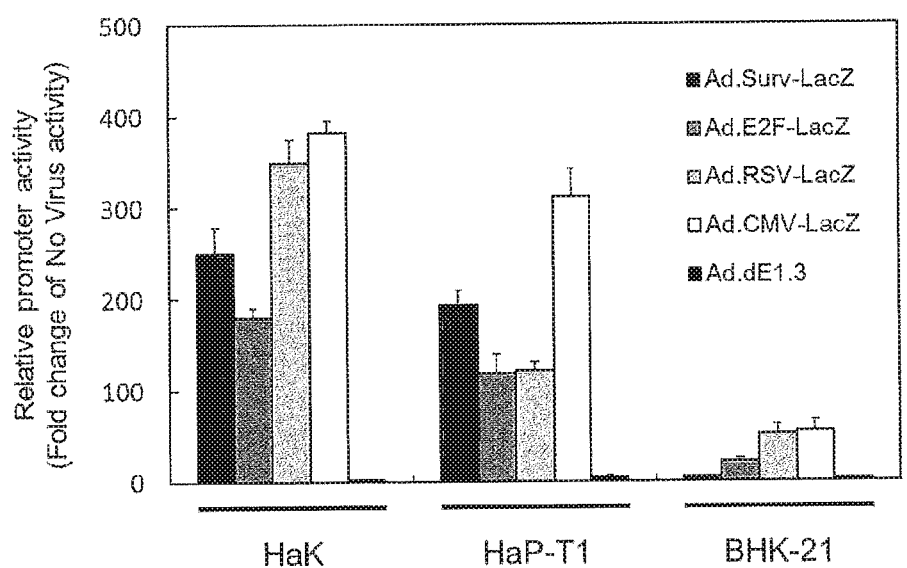
FIG. 4 is a graph showing β-galactosidase activity 48 hours after infection and. gene transfer of hamster derived cancer cells (HaK and HaP-T1) and normal cells (BHK-21) with. Ad.dE1.3 (lacking foreign LacZ gene to be expressed as a control), Ad.E2Fp-LacZ (expressing LacZ under E2F promoter), Ad.RSVp-LacZ (expressing LacZ under RSV promoter), or Ad.Survp-LacZ (expressing LacZ gene under survivin promoter), all of which were "non"-proliferative adenovirus vectors capable of only gene transfer, in order to examine each promoter activity. The ordinate depicts relative β-galactosidase activity to that of infection with the control virus Ad-dE1.3, and the abscissa depicts each line of hamster derived cells.

The results are shown in FIG. 4. The RSV promoter and the CMV promoter exhibited strong activity in the cancer cells (HaK cells), whereas the E2F promoter and the survivin promoter exhibited moderate activity. The moderate activity of the survivin promoter, the E2F promoter, and the RSV promoter was observed in the HaP-T1 cells. On the other hand, almost no activity of the survivin promoter was seen n the normal cells. The other promoters also tended to have low activity in the normal cells compared to the cancer cells, whereas the E2F promoter exhibited lower activity than that of the RSV promoter and the CMV promoter in the normal cells. This demonstrated that the E2F promoter and the survivin promoter exhibit moderate promoter activity in two different types of cancer cells and exhibit much lower activity than that of the RSV promoter and the CMV promoter in the normal cells, i.e., exhibits the characteristics of a cancer cell specific (dominant) promoter.

(Example 4) Mouse GM-CSF Expression in Hamster Cells Infected with mGM-CSF Expression Surv.m-CRA Since no reliable gene sequence of hamster GM-CSF has been reported, mouse GM-CSF (mGM-CSF) was used. The expression level of the mGM-CSF protein in hamster derived cancer cells (HaK and HaP-T1) and normal cells (BHK-21) infected with each mGM-CSF expression Surv.m-CRA was studied by ELISA (Enzyme-Linked ImmunoSorbent Assay). The cells of each line inoculated to a 6-well plate on the day before infection were counted on the day of infection and were consequently HaK: $1.4 \times 10^6$ cells/well, HaP-T1: $1.47 \times 10^6$ cells/well, and BHK-21: $2.2 \times 10^6$ cells/well. The cells were infected with Ad.dE1.3 (control), Surv.m-CRA, Surv.m-CRA/E2Fp-mGM-CSF, Surv.m-CRA/RSVp-mGM-CSF, or Surv.m-CRA/CAp-mGM-CSF under conditions involving MOI of 1, 10, and 100 for 1 hour, and then cultured for 48 hours. Then, the culture supernatants were recovered, and the amount of the mGM-CSF protein expressed was studied using Mouse GM-CSF Quantikine ELISA Kit (R&D Systems, Inc.). The ELISA measurement was conducted in 2 wells per cell supernatant, and the data was indicated by mean±standard deviation. Statistically significant difference among the conditions was studied by Student's t test (*, $P<0.05$). In addition, the same study was conducted on Surv.m-CRA (Surv.m-CRA/E2Fp-hGM-CSF, Surv.h-CRA/RSVp-mGM-CSF, and Surv.m-CRA/CAp-hGM-CSF) each expressing human GM-CSF (hGM-CSF).

Figure 5:
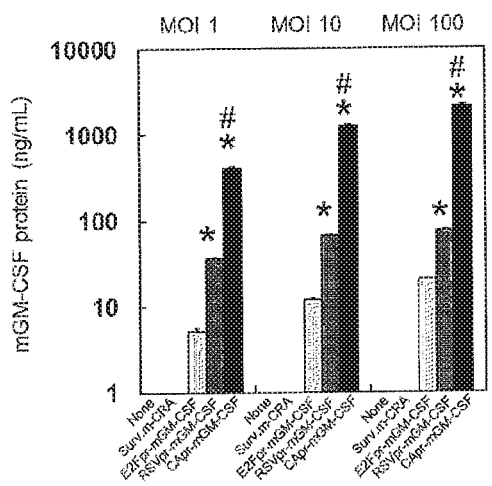
FIG. 5 is a graph showing the amount of GM-CSF protein expressed 48 hours after infection of hamster derived cancer cells (HaK and HaP-T1) and normal cells (BHK-21) with Ad.dE1.3 (control), Surv.m-CRA, Surv.m-CRA/E2Fp-mGM-CSF, Surv.m-CRA/RSVp-mGM-CSF, or Surv.m-CRA/CAp-mGM-CSF. In the drawing, Surv.m-CRA/E2Fp-mGM-CSF, Surv.m-CRA/RSVp-mGM-CSF, and Surv.m-CRA/CAp-mGM-CSF are indicated by the name of the expressed gene, i.e., E2Fp-mGM-CSF, RSVp-mGM-CSF, and CAp-mGM-CSF, respectively, for convenience due to too long designations.
Figure 5:
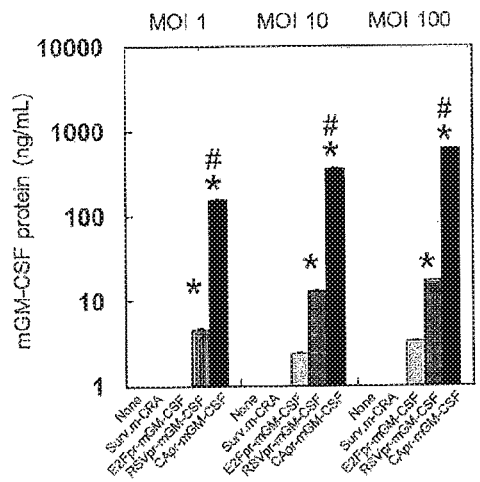
Figure 5:
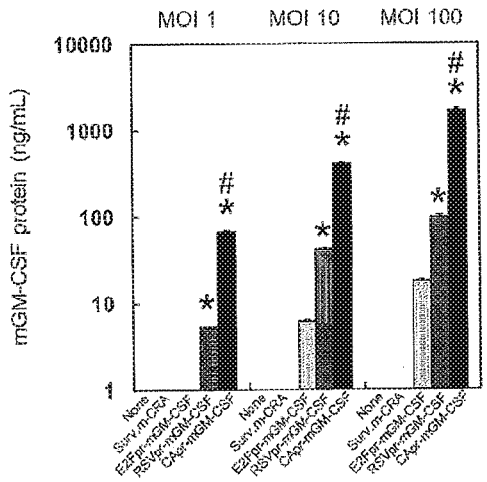
Figure 5:
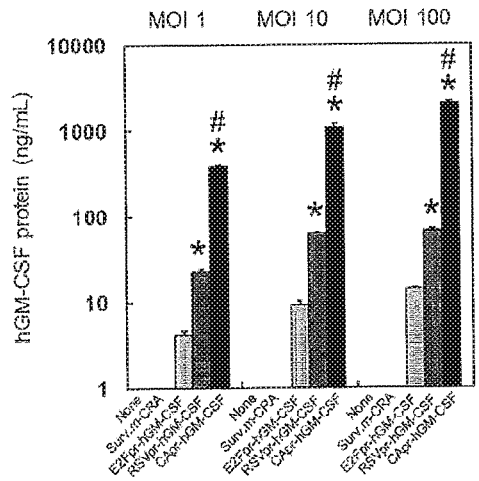

The results are shown in FIG. 5. MOI dependent elevation in mouse GM-CSF expression was observed in all the cells (FIGS. 5A to 5C). The comparison among the promoters showed that the CA promoter most strongly induced expression resulting in a very high level of cytokine secretion, followed by the RSV promoter which strongly induced expression (resulting in a high level of cytokine secretion), whereas E2F induced moderate cytokine expression and secretion. No marked difference in expression level was observed among the cell species. Similar tendency was observed for the expression of human GM-CSF (FIG. 5D). These results (FIGS. 4 and 5) showed that: the RSV and CMV promoters are activated ubiquitously (irrespective of cell species) and relatively strongly; and the E2F promoter exhibits activity slightly lower than or equivalent to that of the survivin promoter and lower than that of RSV or CMV in cancer, and has activity lower than that of RSV or CMV, albeit not so much as survivin, in normal cells, thus exhibiting cancer specificity even weaker than that of the survivin promoter. This revealed for the first time the characteristics of each promoter in hamster cells, specifically, "specific" difference in relative activity levels of these four promoters between cancer cells and normal cells, and their degrees of cancer specific activity.

(Example 5) Cytotoxic Effect of mGM-CSF Expression Surv.m-CRA Infection on Hamster Cell A cytotoxic effect on hamster derived cancer cells (HaK and HaP-T1) and normal cells (BHK-21) infected with each mGM-CSF expression Surv.m-CRA was studied by measuring the number of live cells. The cells of each line were inoculated at $5 \times 10^2$ cells/well to a 96-well plate on the day before infection. The cells were infected with Ad.dE1.3 (control), Surv.m-CRA, Surv.m-CRA/E2Fp-mGM-CSF, Surv.m-CRA/RSVp-mGM-CSF, or Surv.m-CRA/CAp-mGM-CSF at MOI of 3 and 30 for 1 hour, and then cultured. Cytotoxicity was evaluated 3 and 5 days after the infection by WST-8 assay using Live Cell Count Reagent SF (Nacalai Tesque, Inc.).

Figure 6A:
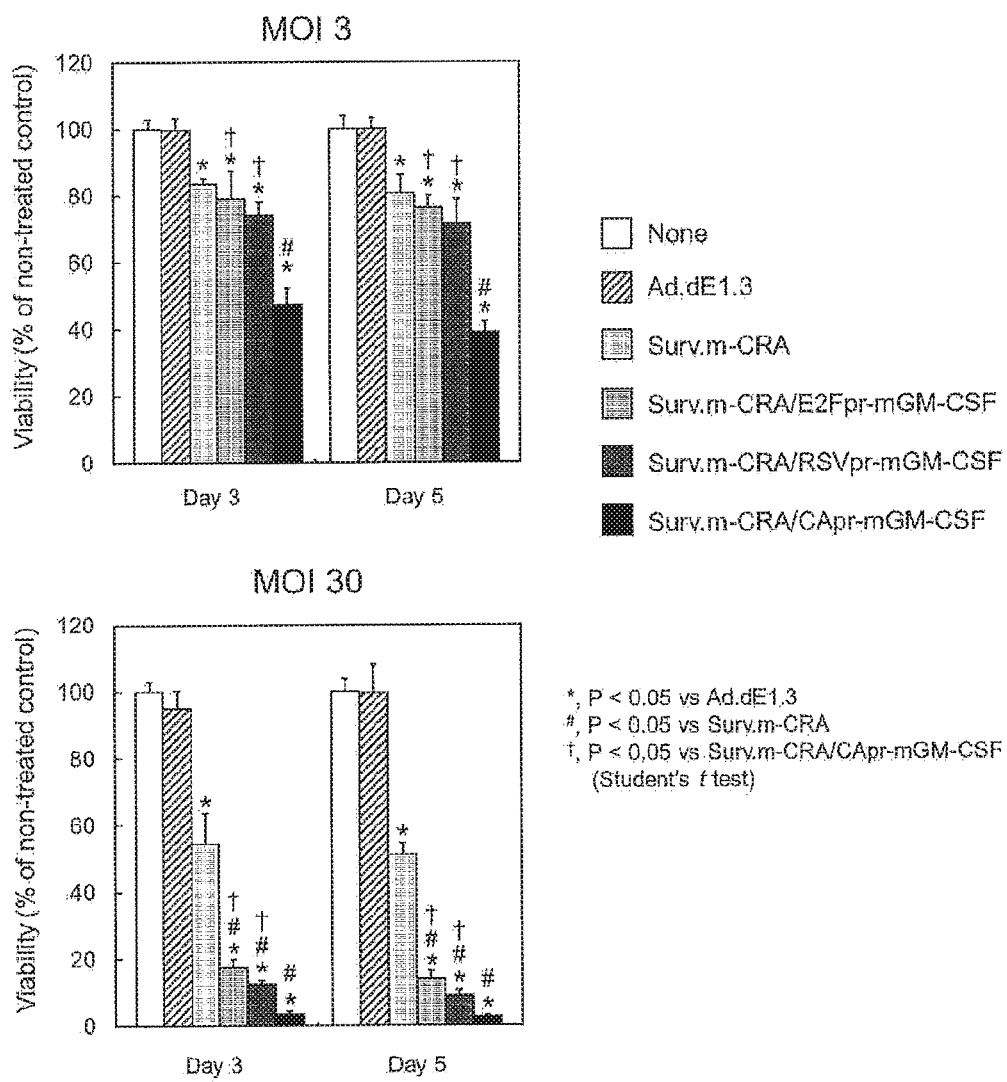
FIG. 6A is a graph showing cytotoxicity 3 days and 5 days after infection of hamster derived cancer cells (HaK) with a "non"-proliferative adenovirus vector Ad.dE1.3 as a control or each oncolytic virus Surv.m-CRA (lacking a therapeutic gene), Surv.m-CRA/E2Fp-mGM-CSF, Surv.m-CRA/RSVp-mGM-CSF, or Surv.m-CRA/CAp-mGM-CSF at MOI3 (upper graph) or MOI30 (lower graph).
Figure 6B:
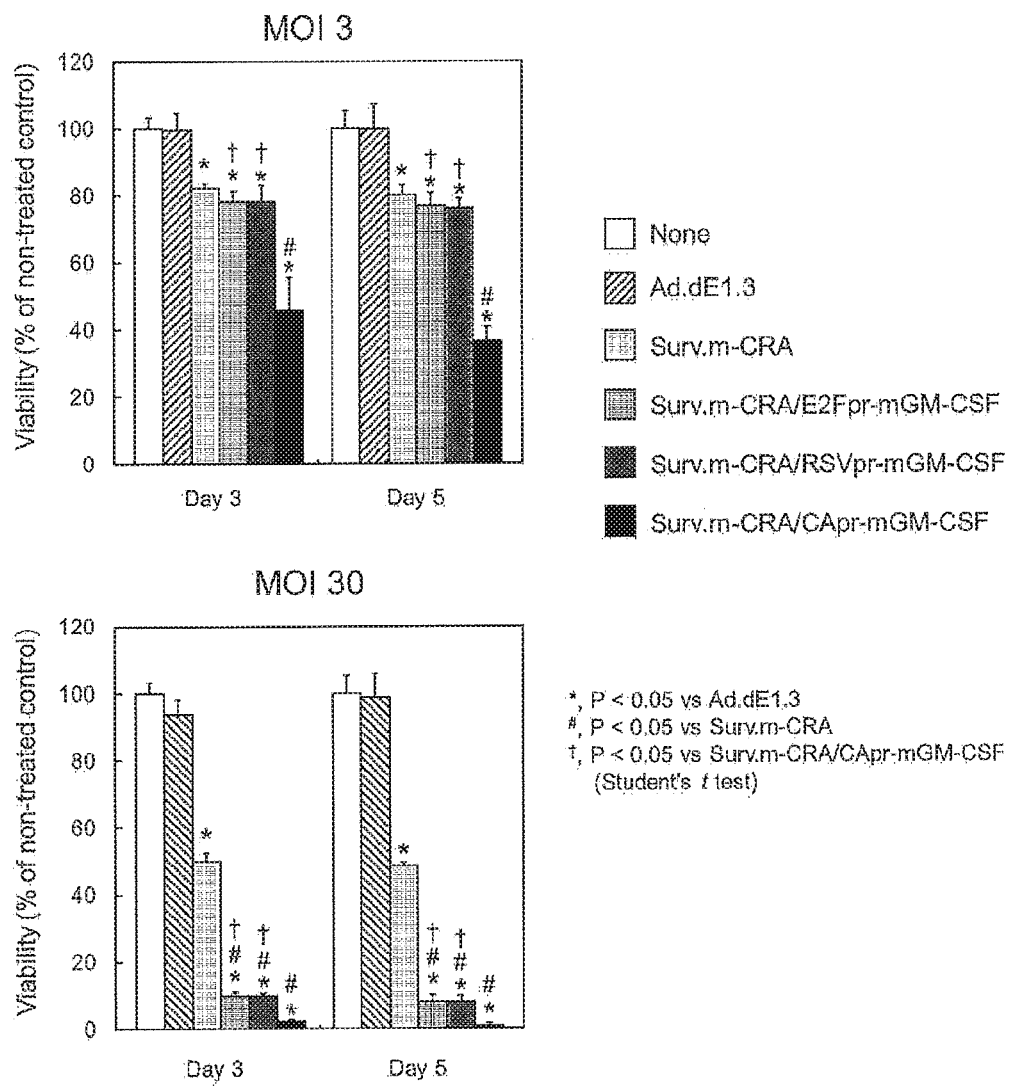
FIG. 6B is a graph showing cytotoxicity 3 days and 5 days after infection of hamster derived cancer cells (HaP-T1) with a "non"-proliferative adenovirus vector Ad.dE1.3 as a control or each oncolytic virus Surv.m-CRA (lacking a therapeutic gene), Surv.m-CRA/E2Fp-mGM-CSF, Surv.m-CRA/RSVp-mGM-CSF, or Surv.m-CRA/CAp-mGM-CSF at MOI3 (upper graph) or MOI30 (lower graph).
Figure 6C:
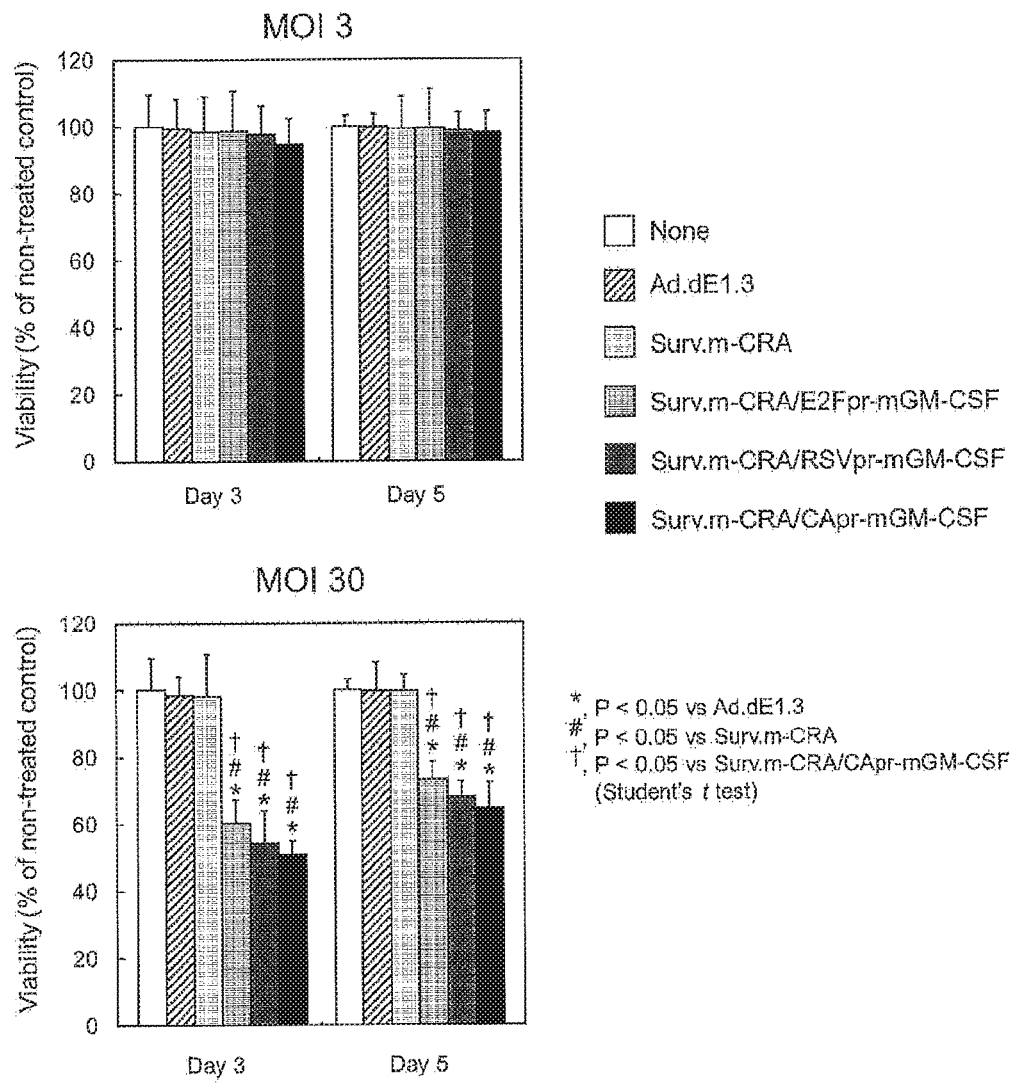
FIG. 6C is a graph showing cytotoxicity 3 days and 5 days after infection of hamster derived normal cells (BHK-21) with a "non"-proliferative adenovirus vector Ad.dE1.3 as a control or each oncolytic virus Surv.m-CRA (lacking a therapeutic gene), Surv.m-CRA/E2Fp-mGM-CSF, Surv.m-CRA/RSVp-mGM-CSF, or Surv.m-CRA/CAp-mGM-CSF at MOI3 (upper graph) or MOI30 (lower graph).

As a result, significant cytotoxic effects of all of Surv.m-CRA and the three types of GM-CSF expression Surv.m-CRA compared to the control were observed in HaK and HaP-T1 (FIG. 6). Significantly high cytotoxic effects of all of the three types of GM-CSF expression Surv.m-CRA3 compared to Surv.m-CRA were also observed. Particularly, the cytotoxic effects were strongest for the CA promoter followed by the RSV promoter, and the cytotoxic effect for E2F was lower than that of CA. Stronger damage was seen at MOI of 30 than at MOI of 3. On the other hand, in BHK-21, a moderate cytotoxic effect was seen in the mGM- CSF expression viruses at MOI of 30, whereas no significant cytotoxic effect was seen in any of the viruses at MOI of 3. This showed that the survivin promoter offers favorable characteristics, i.e., safety based on a high level of cancer specification, of the base (skeleton) Surv.m-CRA, CRA controlling viral proliferation.

Figure 7:
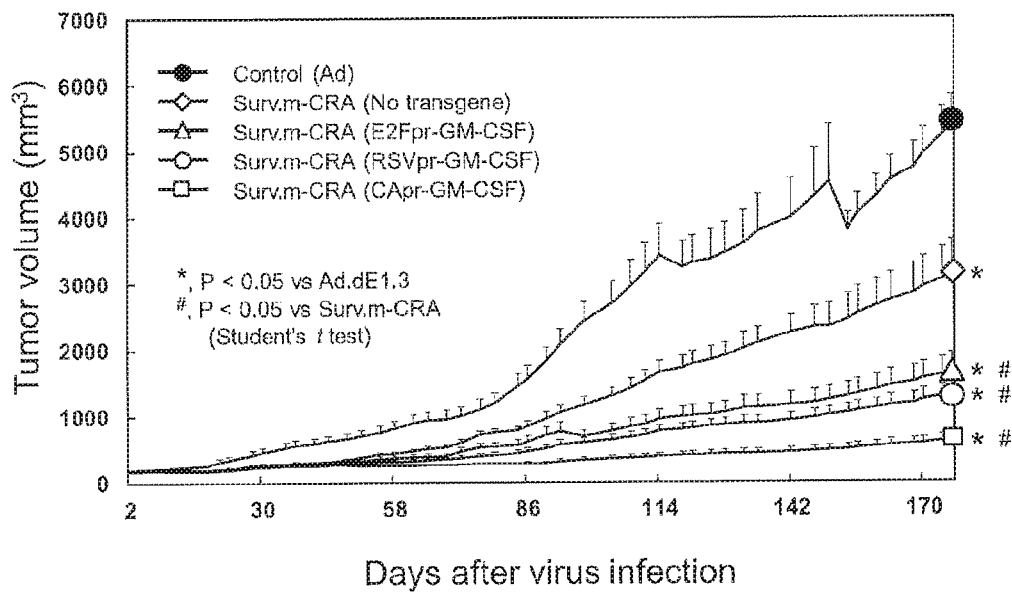
FIG. 7 is a graph showing time dependent change in tumor size after intratumoral single-dose administration of each virus with $1 \times 10^9$ PFU to female 5-week-old. Syrian hamsters in which $1 \times 10^7$ HaK cells were subcutaneously transplanted to the back.

(Example 6) Tumor Suppressive Effect of mGM-CSF Expression Surv.m-CRA in Cancer Bearing Hamster Model $1\times10^7$ HaK cells were subcutaneously transplanted to one site in the back of each female 5-week-old Syrian hamster. In this operation, the HaK cells were prepared into $1\times10^7$ cells/200 μl in 50% Matrigel using Corning® Matrigel basement membrane matrix (Corning Inc.). Approximately 33 days later when the diameter of the transplanted tumor reached 6 to 10 mm, each of the viruses Ad.dE1.3 (control), Surv.m-CRA, Surv.m-CRA/E2Fp-mGM-CSF, Surv.m-CRA/RSVp-mGM-CSF, and Surv.m-CRA/CAp-mGM-CSF was adjusted to $1\times10^9$ RFU/100 μl with PBS, and then intratumorally in by a single dose. Time dependent change in tumor size was evaluated (FIG. 7). The numbers of animals in the groups given the Ad.dE1.3 (control), Surv.m-CRA, Surv.m-CRA/E2Fp-mGM-CSF, Surv.m-CRA/RSVp-mGM-CSF, and Surv.m-CRA/CAp-mGM-CSF viruses were n=12, 9, 11, 11, and 12, respectively. The size of the tumor was measured twice a week using a digital caliper. The tumor volume was calculated according to Major axis (mm)×Minor axis (mm)×Minor axis (mm)×0.5 (mm³). The data was indicated by mean±standard deviation. Statistically significant difference among the groups was studied by Student's t test (*, P<0.05 vs Ad.dE1.3; #, P<0.05 vs Surv.m-CRA).

As a result, all of Surv.m-CRA and the three types of GM-CSF expression Surv.m-CRA compared to the control (Ad.dE1.3) exhibited a significant (strong) therapeutic effect (tumor suppressive effect) on cancer cells (nodal cells) of the treated primary tumor (FIG. 7). All of the three types of GM-CSF expression Surv.m-CRA compared to Surv.m-CRA without therapeutic gene significantly exhibited further "enhancement" in therapeutic effect (tumor suppressive effect).

(Example 7) Survival Curve After mGM-CSF Expression Surv.m-CRA Infection in Cancer Bearing Hamster Model The influence of the single-dose injection of each virus described above on the survival of HaK transplanted hamsters was evaluated by survival curve analysis according to the Kaplan-Meier method. Statistically significant difference among groups was studied by log-rank test.

Figure 8:
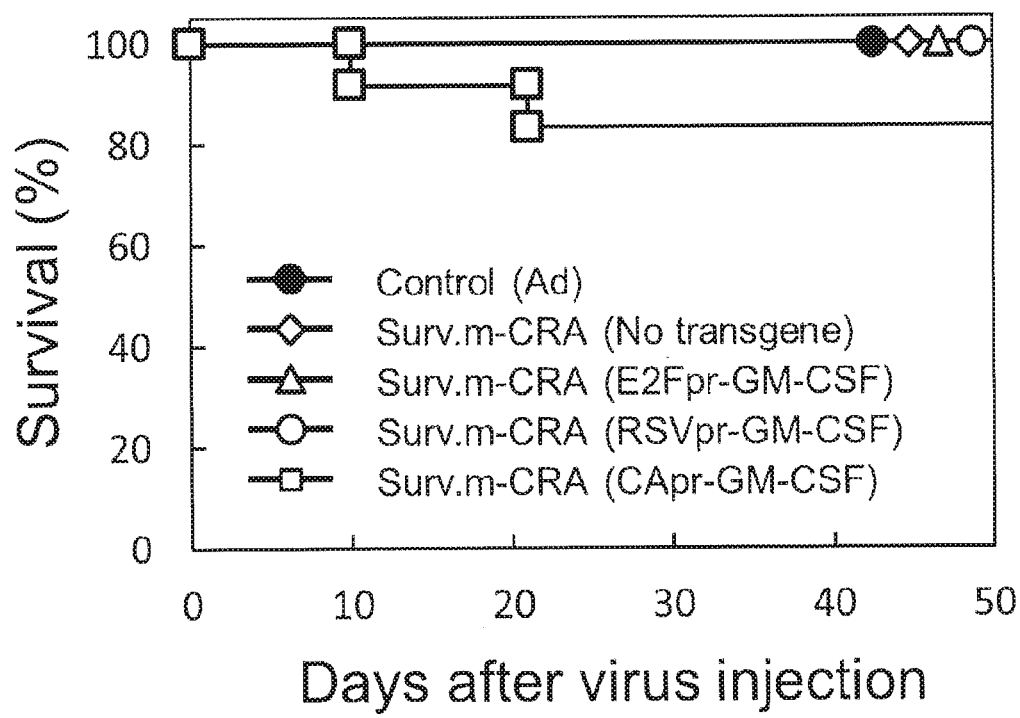
FIG. 8 is a graph showing time dependent change in survival rate after intratumoral single-dose administration of each virus with $1 \times 10^9$ PFU to female 5-week-old Syrian hamsters in which $1 \times 10^7$ HaK cells were subcutaneously transplanted to the back.

As a result, significant difference over the whole period was not observed in between any of the groups (FIG. 8). However, dead cases appeared in the Surv.m-CRA/CAp-mGM-CSF infected group from 10 to 20 days after the infection (FIG. 8). As a result of their autopsy, pulmonary edema or hydrops, enlargement of the spleen, dark cells in the kidney, white spots in the liver, and the like were observed, and the cause of death was confirmed by pathological analysis to be systemic lethal adverse reactions ascribable to abnormality in the immune system associated with cytokine overexpression. These experimental results confirmed again the necessity of the optimal expression level of GM-CSF. Specifically, the present experiment revealed for the first time for promoters, such as CA, E2F, and RSV, conventionally regarded vaguely as "strongly active promoters" that: CA has much stronger promoter activity than that of E2F; and the CA promoter brings about lethal adverse reactions and is not suitable for use, particularly, in the control of an immunity-inducing gene carried in an oncolytic virus, whereas the E2F promoter, despite inducing moderate expression, is an "optimal (moderate degree of)" promoter that insures high safety while exhibiting a strong therapeutic effect. In short, the present experiment discovered the new concept that "there exists an optimal (moderate degree of) promoter for the control of an immunity-inducing gene carried in an oncolytic virus" and also discovered a specific invention disclosing that the expression level induced by the E2F promoter is optimal for this system.

(Example 8) Re-Challenge Test on Hamster After Treatment with mGM-CSF Expression Surv.m-CRA $1\times10^7$ HaK cells were subcutaneously transplanted to one site in the back of each female 5-week-old Syrian hamster. In this operation, the cells were prepared into $1\times10$ cells/200 μl in 50% Matrigel using Corning® Matrigel basement membrane matrix (Corning Inc.). Approximately 28 days later when the diameter of the transplanted tumor reached 6 to 10 mm, each of the viruses Ad.dE1.3 (control), Surv.m-CRA, Surv.m-CRA/E2Fp-mGM-CSF, Surv.m-CRA/RSVp-mGM-CSF, and Surv.m-CRA/CAp-mGM-CSF was adjusted to $1\times10^9$ PFU/100 μl with PBS, and then intratumorally injected by a single dose. The numbers of animals in the groups given the Ad-dE1.3 (control), Surv.m-CRA, Surv.m-CRA/E2Fp-mGM-CSF, Surv.m-CRA/RSVp-mGM-CSF, and Surv.m-CRA/CAp-mGM-CSF viruses were n=4, 5, 4, 3, and 3, respectively. 14 days after the virus injection, $7.5\times10^6$ cells each of HaK and HaP-T1 were prepared into $7.5\times10^6$ cells/200 μl in 50% Matrigel and then subcutaneously transplanted to the back. 15 days later, the formation of secondarily transplanted tumor was evaluated.

The results are shown in Table 1 below. Tumor formation by the retransplantation of HaK was not observed in the groups treated with the three types of GM-CSF expression Surv.m-CRA, whereas tumor formation by the transplantation of HaP-T1 was observed in all the cases. In the groups treated with the control (Ad.dE1.3) or Surv.m-CRA, tumor formation by the secondary transplantation of HaK or HaP-T1 was observed in all the cases. These results demonstrated that in the groups treated with mGM-CSF expression Surv.m-CRA, use of even the moderate promoter such as E2F promoter can induce HaK (treated cancer cells) specific systemic antitumor immunity, as in use of a strong promoter such as CA, strongly blocking (treating) metastatic cancer cells.

TABLE 1

Analysis of systemic antitumor immunity induction by challenge test

| | Re-challenged cancer cell type | |
|---|---|---|
| Virus | Parental (HaK) | Other (HaP-T1) |
| Control (Ad) | 4/4 (100%) | 5/5 (100%) |
| Surv.m-CRA (No transgene) | 5/5 (100%) | 5/5 (100%) |
| Surv.m-CRA (E2Fp-mGM-CSF) | 0/4 (0%) | 4/4 (100%) |

TABLE 1-continued

Analysis of systemic antitumor immunity induction by challenge test

| Virus | Re-challenged cancer cell type | |
|---|---|---|
| | Parental (HaK) | Other (HaP-T1) |
| Surv.m-CRA (RSVp-mGM-CSF) | 0/3 (0%) | 3/3 (100%) |
| Surv.m-CRA (CAp-mGM-CSF) | 0/3 (0%) | 3/3 (100%) |

Tumore formation: animal # (%)

(Example 9) Study on Amount of mGM-CSF Expressed within Tissue After Infection of Cancer Bearing Hamster Model with mGM-CSF Expression Surv.m-CRA $1\times10^7$ HaK cells were subcutaneously transplanted to one site in the back of each female 5-week-old Syrian hamster. In this operation, the cells were prepared into $1\times10^7$ cells/200 µl in 50% Matrigel using Corning® Matrigel basement membrane matrix (Corning Inc.). Approximately 42 days later when the diameter of the transplanted tumor reached 6 to 10 mm, each of the viruses Ad.dE1.3 (control), Surv.m-CRA, Surv.m-CRA/E2Fp-mGM-CSF, Surv.m-CRA/RSVp-mGM-CSF, and Surv.m-CRA/CAp-mGM-CSF was adjusted to $1\times10^9$ PFU/100 µl with PBS, and then intratumorally injected by a single dose. Then, serum, tumor, and the spleen were isolated 2 and 7 days later, and the expression level of mGM-CSF within the tissue was studied by ELISA. The number of animals in each group given the virus was n=3 on each day. The data was indicated by mean±standard deviation. Statistically significant difference among the groups was studied by Student's t test (*, P<0.05 vs Surv.m-CRA/E2Fpr-mGM-CSF; #, P<0.05 vs Surv.m-CRA/RSVpr-mGM-CSF).

Figure 9:
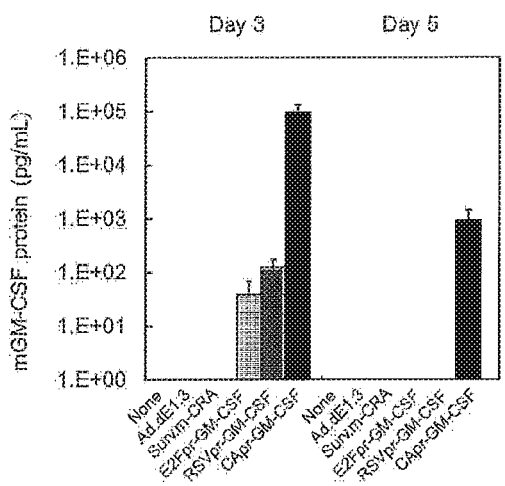
FIG. 9 is a graph showing the amount of mGM-CSF expressed within a tissue after infection of cancer bearing hamster models with mGM-CSF expression Surv.m-CRA.
Figure 9:
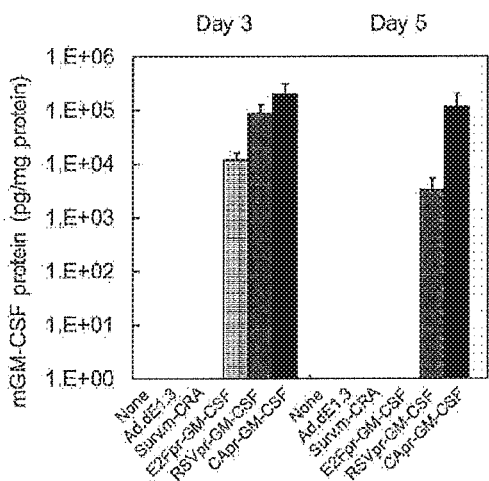
Figure 9:
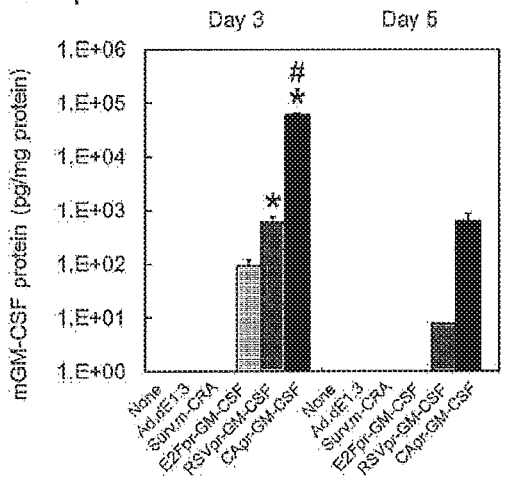
Figure 10:
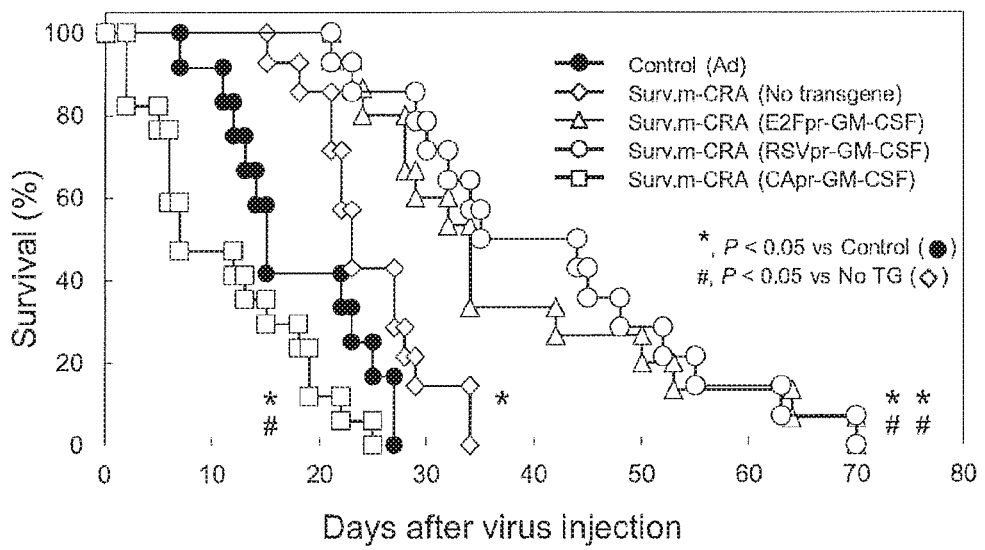
FIG. 10 is a graph showing a survival curve after infection of orthotopic cancer bearing hamster models with mGM-CSF expression Surv.m-CRA.
Figure 11:
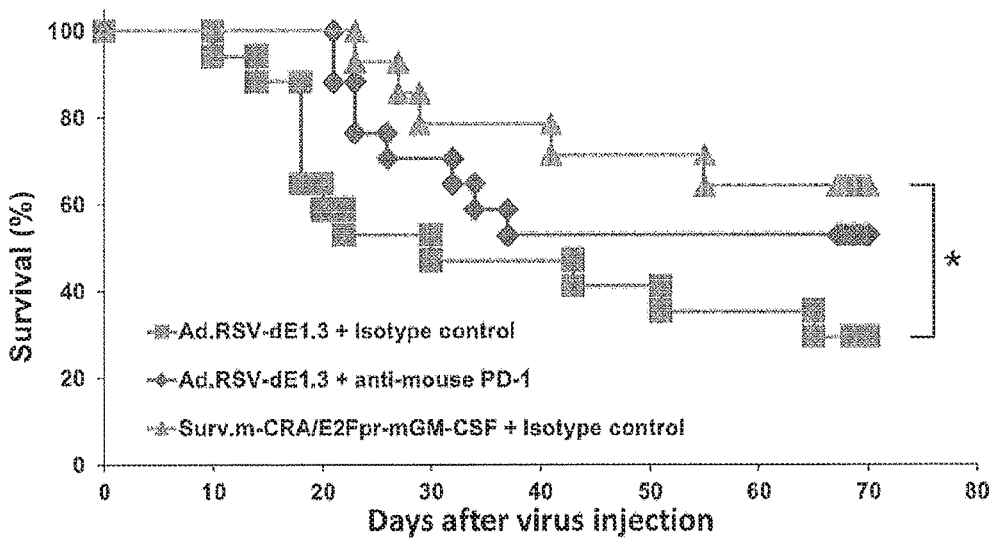
FIG. 11 is a graph showing a survival curve after infection of orthotopic cancer bearing hamster models with mGM-CSF expression Surv.m-CRA or after administration of an anti-PD-1 antibody.
Figure 12:
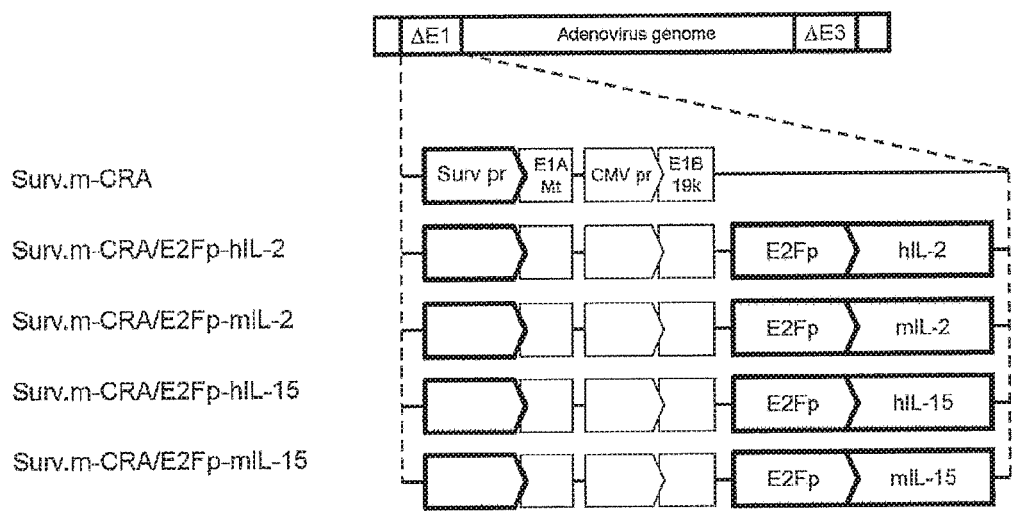
FIG. 12 is a schematic view of IL-2 or IL-15 expression Surv.m-CRA having an insert of an expression cassette of mouse or human IL-2 or IL-15 cDNA linked to each promoter (E2F promoter, RSV promoter, and CA promoter) in Surv.m-CRA containing survivin promoter incorporated upstream of E1A, an early gene essential for adenovirus proliferation.

As a result, a significant mGM-CSF expression level was observed in all of the three types of GM-CSF expression Surv.m-CRA compared to the control (Ad.dE1.3) (FIG. 9). Particularly, the amount of mGM-CSF expressed within the serum on day 2 for the CA promoter exhibited a high value 1000 or more times the value for the other two promoters. Accordingly, these results more clearly demonstrated that the cause of early death observed in the Surv.m-CRA/CAp-mGM-CSF infected group in FIG. 8 was an abnormal and pathological level of systemic immune activation ascribable to cytokine overexpression. Surprisingly, the E2F promoter was found to exert effects such as high antitumor activity and prolongation of survival periods as mentioned above, though bringing about the expression of GM-CSF only in an amount lower than the detection limit on the 5th day in all of the serum, the tumor, and the spleen.

(Example 10) Survival Curve After mGM-CSF Expression Surv.m-CRA Infection in Orthotopic Cancer Bearing Hamster Model $1\times10^7$ hamsters kidney cancer derived HaK cells were transplanted to one kidney of each female 5-week-old Syrian hamster. In this operation, the cells were prepared into $1\times10^7$ cells/200 µl in 50% Matrigel using Corning® Matrigel basement membrane matrix (Corning Inc.). Approximately 14 days later, each of the viruses Ad.dE1.3 (control), Surv.m-CRA, Surv.m-CRA/E2Fp-mGM-CSF, Surv.m-CRA/RSVp-mGM-CSF, and Surv.m-CRA/CAp-mGM-CSF was adjusted to $1\times10^9$ PFU/100 µl with FBS, and then injected into the tumor transplanted kidney by a single dose. Then, the influence of the single-dose injection of each virus described above on the survival of the orthotopic cancer bearing hamster models was evaluated by survival curve analysis according to the Kaplan-Meier method. Statistically significant difference among the groups was studied by log-rank test.

As a result, dead cases caused by the adverse reaction of systemic pathological (abnormal) immune activity associated with cytokine overexpression appeared in the Surv.m-CRA/CAp-mGM-CSF group, as in the subcutaneous tumor models, from 5 to 10 days after the infection (at the early stage of treatment). Thus, survival rates were significantly shortened, i.e., death rates were significantly elevated, as compared with the Ad.dE1.3 (control) and Surv.m-CRA groups. Interestingly, very prominent and significant prolongation of survival was observed in the groups given Surv.m-CRA/E2Fp-mGM-CSF or Surv.m-CRA/RSVp-mGM-CSF compared not only to the Surv.m-CRA/CAp-mGM-CSF group but to the Ad.dE1.3 (control: non-proliferative adenovirus) and Surv.m-CRA (therapeutic gene uncarried) groups. However, no significant difference was observed between the Surv.m-CRA/E2Fp-mGM-CSF group and the Surv.m-CRA/RSVp-mGM-CSF group. It is particularly to be noted that the present invention revealed for the first time that: a mere suppressive effect on tumor enlargement in subcutaneous tumor models (which are generally used in simple and easy experimental systems) has no significant difference among the therapeutic effects of Surv.m-CRA/E2Fp-mGM-CSF, Surv.m-CRA/RSVp-mGM-CSF, and Surv.m-CRA/CAp-mGM-CSF, whereas Surv.m-CRA/E2Fp-mGM-CSF and Surv.m-CRA/RSVp-mGM-CSF exhibit very high efficacy in the analysis of long-term survival rates in orthotopic tumor models which permit actual clinical evaluation of the usefulness of a final therapeutic drug for cancer in humans, and reflect pathological conditions; however, Surv.m-CRA/CAp-mGM-CSF rather has poor efficacy (lethal and dangerous). As also shown in FIG. 9, the RSV promoter has the possibility of bringing about adverse reactions that do not appear in survival, because GM-CSF was expressed at a level detected in the spleen on the 5th day, albeit at a level lower than that by the CA promoter. Accordingly, the present experiment revealed for the first time that the optimal expression level for mounting an immunity-inducing gene in an oncolytic virus not only drastically improves safety but enhances the therapeutic effect itself. The present experiment further revealed for the first time that a promoter that can achieve the optimal expression level is E2F promoter or a promoter that brings about an expression level equivalent thereto.

(Example 11) Comparison of Survival Curve Between After mGM-CSF Expression Surv.m-CRA Infection and After Anti-Mouse PD-1 Antibody Administration in Orthotopic Cancer Bearing Hamster Model 1×10 hamsters kidney cancer derived HaK cells were transplanted to one kidney of each female 5-week-old Syrian hamster. In this operation, the cells were prepared into $1\times10^7$ cells/200 µl in 50% Matrigel using Corning® Matrigel basement membrane matrix (Corning Inc.). Approximately 14 days later, each of the viruses Ad.dE1.3 (control) and Surv.m-CRA/E2Fp-mGM-CSF was adjusted to 1×109 PFU/100 µl with FBS, and then injected into the tumor transplanted kidney by a single dose. On the same day therewith, 500 µg of an anti-mouse PD-1 antibody or an isotype control antibody was intraperitoneally administered to each hamster. This day was defined as day 0, and the same amount of the same antibody as in the day 0 was also administered on days 2, 4, 6, and 8. Then, influence on survival was analyzed in the same way as above.

As a result, survival rates were significantly prolonged, i.e., death rates were significantly decreased, in the Surv.m-CRA/E2Fpr-mGM-CSF group (N=14) compared to the Ad.dE1.3 (control) group (N=17). A tendency of equivalent or greater prolongation of survival rates was exhibited as compared with the anti-mouse PD-1 antibody administration group (N=17).

When the results of all these Examples are taken together, the present invention has discovered for the first time the concept itself that "for the oncolytic immunotherapeutic agent (oncolytic virus with immunity-inducing gene), accurate control of the optimal expression level of the immunity-inducing factor is essential for both the purposes of drastically ensuring safety (removing lethal adverse reactions) and inducing a strong therapeutic effect, because the carried immunity-inducing gene is amplified together with the virus". None of the previous inventions not only clearly show this concept in terms of "safety" but suggest this concept in terms of "drastic enhancement in therapeutic effect". Rather, this concept demolishes vague ungrounded dogma (enhanced expression of a therapeutic gene elevates the therapeutic effect itself). The present invention has also specifically disclosed a promoter inducing the "optimal (moderate degree of)" expression of an immunity-inducing gene in an oncolytic virus in terms of both safety and a therapeutic effect, and developed a revolutionary therapeutic drug for cancer having performance excelling both the safety and therapeutic effect of conventional oncolytic immunotherapeutic agents. In the previous investigator initiated clinical studies of the inventor, mere Surv.m-CRA without therapeutic gene has been found not only to be very safe but to have a therapeutic effect (increasingly proved in actual human patients) in all cases of refractory cancer that does not respond to previous standard treatment (previous therapeutic drugs for cancer or methods for treating cancer). Therefore, the novel oncolytic immunotherapeutic agent developed by the present invention and the method using the same are expected to offer a more promising and innovative therapeutic drug for cancer.

The invention claimed is:

1. An oncolytic virus comprising an immunity-inducing gene operably linked to and downstream of an E2F promoter (E2Fp),
and at least one viral promoter operably linked to a nucleic acid encoding an element essential for viral replication or assembly, wherein said viral promoter is replaced with a survivin promoter, and wherein the immunity-inducing gene comprises GM-SCF.

2. The oncolytic virus of claim 1, wherein the oncolytic virus is adenovirus.

3. The oncolytic virus of claim 2, wherein the element essential for viral replication or assembly is selected from a group consisting of E1A, E1AΔ24, E1B and E1BΔ55K.

4. The oncolytic virus of claim 2, wherein the at least one element essential for viral replication or assembly is E1A.

5. The oncolytic virus of claim 1, which further comprises an expression cassette including nucleic acids encoding a cytotoxic factor or a therapeutic factor operably linked to an exogeneous promoter.

6. A therapeutic agent for cancer, comprising the oncolytic virus of claim 1.

7. A method of treatment of cancer, comprising administration of the oncolytic virus of claim 1, wherein the method results in less damage to non-targeted cells.

* * * * *